United States Patent

Kawashima et al.

Patent Number: 5,556,841
Date of Patent: Sep. 17, 1996

[54] THIAZINE OR THIOMORPHOLINE DERIVATIVES

[75] Inventors: Yoichi Kawashima, Kyoto; Atsutoshi Ota; Hiroyuki Mibu, both of Osaka, all of Japan

[73] Assignee: Santen Pharmaceutical Co., Ltd., Osaka, Japan

[21] Appl. No.: 378,502

[22] Filed: Jan. 26, 1995

[30] Foreign Application Priority Data

Feb. 4, 1994 [JP] Japan ........................... 6-12979

[51] Int. Cl.$^6$ ............. C07D 279/10; C07D 179/12; A61K 31/54; A61K 31/425
[52] U.S. Cl. ............. 514/61; 514/90; 514/227.5; 514/227.8; 544/57; 544/58.2; 544/58.4; 544/60; 544/56; 544/59
[58] Field of Search ............. 514/227.5, 227.8, 514/61, 90; 544/57, 58.2, 58.4, 60, 59, 56

[56] References Cited

FOREIGN PATENT DOCUMENTS

0162776A2  11/1985  European Pat. Off. .
0492667A1   7/1992  European Pat. Off. .
0627425A1  12/1994  European Pat. Off. .
 627425    12/1994  European Pat. Off. .

OTHER PUBLICATIONS

Patent Abstracts Of Japan, vol. 9, No. 205 (C–200) [1928], 22 Aug. 1985 of JP-A-60 072876 (Hammari Yakuhin Kogyo K. K.), 24 Apr. 1985.
Patent Abstracts Of Japan, vol. 14, No. 63 (C–685) [4006], 6 Feb. 1990 of JP-A-01 287077 (Santen Pharmaceut. Co. Ltd), 17 Nov. 1989.
Chemical Abstracts, vol. 84, No. 15, 12 Apr. 1976, Columbus, Ohio, US; abstract No. 105612P, p. 583; column 1 of JP-A-50 126 677 (Yoshitomi Pharmaceuticals Industries, Ltd.), 4 Oct. 1975.
Chemical Abstracts, vol. 84, No. 15, 12 Apr. 1976, Columbus, Ohio, US; abstract No. 105613q, p. 583; column 1 of JP-A-50 126 676 (Yoshitomi Pharmaceutical Industries, Ltd.), 4 Oct. 1975.
Opthalmology, 19, 1283–1296, (1977).
Biochimica et Biophysica Acta, 489, 163–172, (1977) Shimeda et al.
Jap. J. Opthalmol., 20, 399–410, (1976) Kinoshita et al.
Invest. Ophthalmol., 13, 713–724, (1974) Kinoshita et al.
Chem. Pharm. Bull., 33, 74–83, (1985) Kato et al.
Current Eye Research, 5, No. 1, 37–40 (1986) Nishigori et al.

Primary Examiner—Mukund J. Shah
Assistant Examiner—Matthew V. Grumbling
Attorney, Agent, or Firm—Frishauf, Holtz, Goodman, Langer & Chick, P.C.

[57] ABSTRACT

This invention relates to the compounds of the formula [I] which are useful for the treatment of cataracts, and the synthetic intermediates of the formula [II],

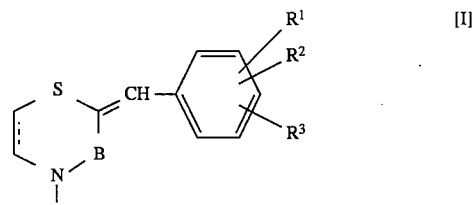

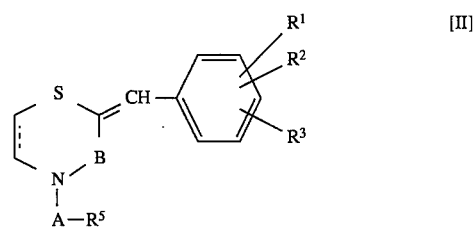

wherein $R^1$ is hydroxy which can be protected by a hydroxy protective group;

$R^2$ is lower alkyl;

$R^3$ is hydrogen, lower alkyl, hydroxy, which can be protected by a hydroxy protective group, or lower alkoxy, and the said lower alkyl can be substituted by hydroxy, which can be protected by a hydroxy protective group, amino or lower alkylamino;

$R^4$ is carboxy which can be converted into ester or amide; tetrazolyl; phosphono which can be converted into ester or amide; or sulfonyl which can be converted into ester or amide;

$R^5$ is cyano or lower alkoxy;

A is alkylene;

B is C=O, C=S or $CH_2$, and

⸗ is single bond or double bond.

40 Claims, No Drawings

THIAZINE OR THIOMORPHOLINE DERIVATIVES

FIELD OF THE INVENTION

This invention relates to novel thiazine or thiomorpholine derivatives which have protein stabilizing effect and suppressive effect on lipid peroxide formation, and are useful for treatment of cataracts etc.

BACKGROUND OF THE INVENTION

The formation of cataracts is an intractable eye condition where an opacification of the lens is caused and which results in a loss of visual acuity. Various studies on a causal factor and mechanism of cataracts, and a treatment method therefor have been made. But at present, there are very few medical substances which are effective for cataracts.

It is reported that an increase of peroxide in the lens is related to a cause of cataracts and a chemical substance having suppressive effect on lipid peroxide formation is effective on treatment of cataracts (Current Eye Res., 5, 37 (1986)). It is also reported that protein denaturation is observed in lenses of cataract patients (Ophthalmology, 19, 1283 (1977)).

From the reports, a chemical substance which has suppressive effect on lipid peroxide formation in combination with protein stabilizing effect can be presumed to be especially useful for treatment of cataracts. A compound having the above both effects, however, has not been studied and the development of such a compound has been desired.

As the result of our precise study to find a compound having a suppressive effect on lipid peroxide formation in combination with a protein stabilizing effect, the inventors found that 1,4-thiazine or thiomorpholine derivatives, wherein the 2nd-position was substituted by a benzylidene group which was further substituted by hydroxy and lower alkyl groups and the 4th-position was substituted by an acidic group such as carboxy, tetrazolyl, phosphono or sulfonyl, exhibited both effects.

Some of 1,4-thiazine or thiomorpholine derivatives having a benzylidene substituent at the 2nd-position, where the chemical structure is common to the basic structure of the compounds of this invention, were reported to show an anti-allergic effect or tyrosinekinase inhibitory effect (Japanese Unexamined Patent Publication No. 29570/1987) or an ultraviolet light absorption effect (Japanese Unexamined Patent Publication No. 126676/1975 and 126677/1975). The description in the publications, however, is limited to 1,4-thiazine or thiomorpholine derivatives wherein the nitrogen atom, that is the 4-th position of the 1,4-thiazine or thiomorpholine ring, has no substituent or has a substituent of alkyl or aralkyl. Further the prior art discloses neither a protein stabilizing effect nor a suppressive effect on lipid peroxide formation.

Some of 2-benzylidene-3-oxo-1,4-benzothiazine derivatives having a ring system formed by a condensation of a thiazine ring and a phenyl ring were reported to show an active oxygen elimination effect or a suppressive effect on lipid peroxide formation (Japanese Unexamined Patent Publication No. 287077/1989).

In the meantime, recently the utility of aldose reductase inhibitors for treatment of cataract has attracted attention. The compound of this invention also has an aldose reductase inhibiting effect and is very useful for the treatment of cataracts.

DETAILED DESCRIPTION OF INVENTION

This invention relates to the compounds of the formula [I] and salts thereof (hereinafter called the compounds of this invention), pharmaceutical use for treatment of cataracts and synthetic intermediates of the formula [II](hereinafter called the intermediates of this invention).

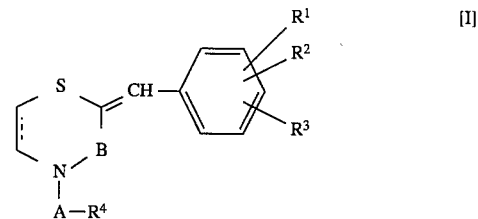

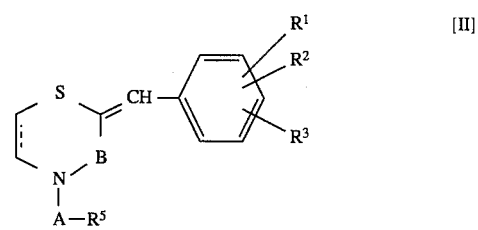

wherein $R^1$ is hydroxy which can be protected by a hydroxy protective group;

$R^2$ is lower alkyl;

$R^3$ is hydrogen, lower alkyl, hydroxy, which can be protected by a hydroxy protective group, or lower alkoxy, and the said lower alkyl can be substituted by hydroxy, which can be protected by a hydroxy protective group, amino or lower alkylamino;

$R^4$ is carboxy which can be converted into ester or amide; tetrazolyl; phosphono which can be converted into ester or amide; or sulfonyl which can be converted into ester or amide;

$R^5$ is cyano or lower alkoxy;

A is alkylene;

B is C=O, C=S or $CH_2$, and

⚌ is single bond or double bond.

The same shall be applied hereinafter.

The terms used in the specification are explained as follows in more detail.

The term "lower alkyl" means straight or branched alkyl having 1 to 6 carbon atoms exemplified by methyl, ethyl, propyl, hexyl, isopropyl and tert.-butyl.

The term "lower alkoxy" means straight or branched alkoxy having 1 to 6 carbon atoms exemplified by methoxy, ethoxy, propoxy, hexyloxy, isopropoxy and tert.-butoxy.

The term "lower alkanoyl" means straight or branched alkanoyl having 2 to 6 carbon atoms exemplified by acetyl, propionyl and pivaloyl.

The term "alkylene" means straight or branched alkylene having 1 to 10 carbon atoms exemplified by methylene, ethylene, propylene, tetramethylene, hexamethylene, heptamethylene, decamethylene, (dimethyl)methylene and (diethyl)methylene.

The term "hydroxy protective group" means a group widely used for protection of a hydroxy group, for example, lower alkylsulfonyl exemplified by methanesulfonyl; arylsulfonyl exemplified by phenylsulfonyl and p-toluenesulfonyl; lower alkanoyl exemplified by acetyl, propionyl and pivaloyl; lower alkoxymethyl exemplified by methoxymethyl; benzoyl; benzyloxymethyl; tetrahydropyranyl, or trimethylsilyl.

The term "ester" means a widely used ester, for example, lower alkyl ester exemplified by methyl ester, ethyl ester, isopropyl ester, butyl ester and hexyl ester, or aryl lower alkyl ester exemplified by benzyl ester.

The term "amide" means a widly used amide, for example, an amide with ammnonia, an amide with lower alkyl amine exemplified by methylamine, dimethylamine and ethyl amine, or an amide with aryl lower alkyl amine exemplified by benzylamine.

The term "aryl" means aromatic hydrocarbon exemplified by phenyl, naphthyl and pyridyl which can be substituted by lower alkyl, etc.

Examples of the pharmaceutically acceptable salts in this invention are alkali metal salts or alkaline earth metal salts exemplified by sodium, potassium and calcium salts, ammonium salt, organic amine salts exemplified by diethylamine and triethanolamine salts, or salts of inorganic acid exemplified by hydrochloric acid, sulfuric acid and nitric acid.

Typical synthetic methods of the compounds of this invention are shown in the following 1)–4).

1) Synthesis of a compound wherein $R^4$ is represented by carboxy which can be converted into ester or amide.

the reaction below.

First, the compound of the formula [V] is prepared by a reaction of the compound of the formula [III] with the compound of the formula [IV] in a presence of base. Second, the hydroxy group of the compound of the formula [V] is protected by an usual method to give the compound of the formula [VI]. Finally, the compound of the formula [VI] is reacted with the compound of the formula [VII] in a presence of base and followed by a removal of the protective group by an usual method to give the compound of the formula [IX] of this invention.

The compound of the formula [IX] of this invention can be also prepared by a reaction of the compound of the formula [VIII], which can be prepared by a dehydration of the compound of the formula [V], with the compound of the formula [VII] in a presence of base.

In another way, the compound of the formula [VIII] can be synthesized according to the method described in Japanese Unexamined Patent Publication No.29570/1987.

2) Synthesis of a compound wherein $R^4$ is represented by tetrazolyl.

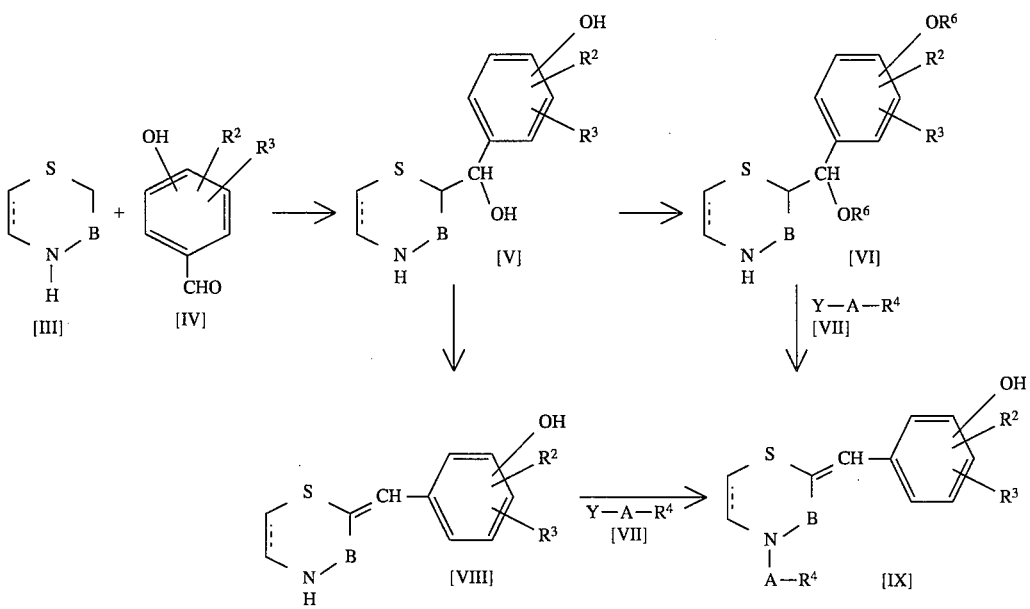

wherein $R^6$ is lower alkanoyl or benzoyl, and Y is halogen, alkylsulfonyl or arylsulfonyl. The same definition applies to

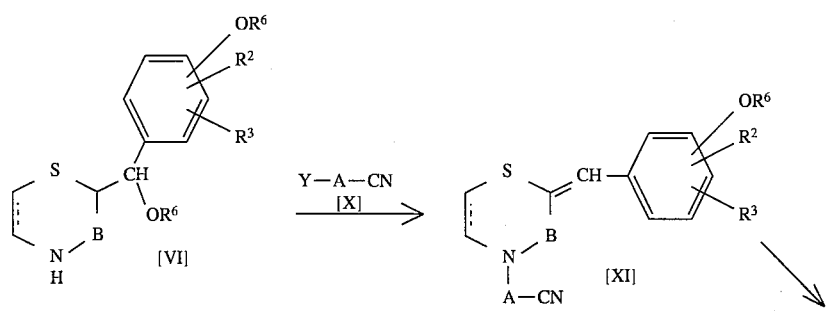

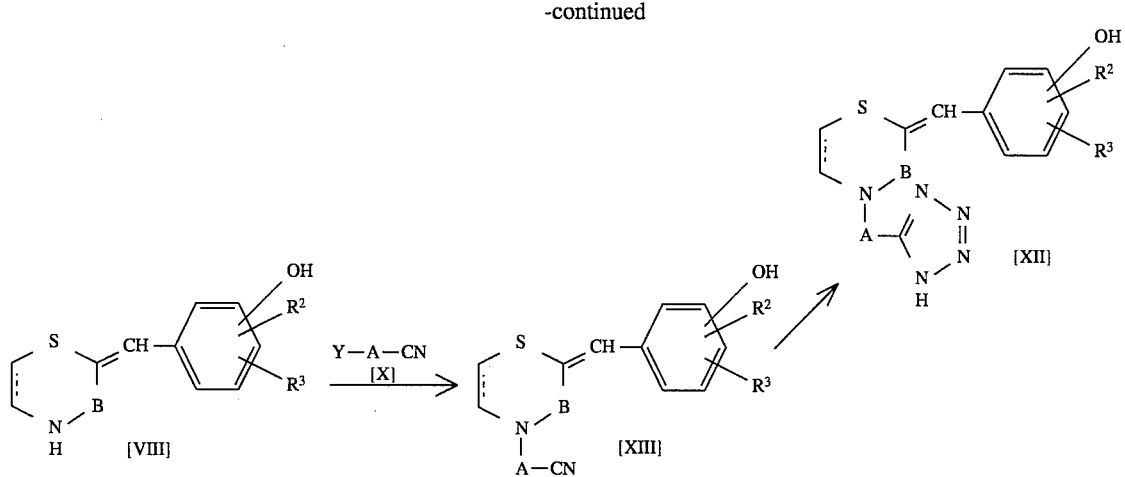

The compound of the formula [XI] is prepared by a reaction of the compound of the formula [VI] with the compound of the formula [X] in a presence of base. The compound of the formula [XI] is further reacted with sodium azide to give the compound of this invention represented by the formula [XII].

In another way, the compound of the formula [XII] of this invention can be also prepared by a reaction of the compound of the formula [XIII], which can be prepared by a reaction of the compound of the formula [VIII] with the compound of the formula [X] in a presence of base, with sodium azide.

The compound of the formula [XI] or [XIII] is also a novel compound which is especially useful as a synthetic intermediate to introduce a tetrazolyl group into $R^4$.

3) Synthesis of a compound wherein $R^4$ is represented by phosphono which can be converted into ester or amide.

wherein $R^7$ is lower alkoxy, and $R^8$ or $R^9$ is hydroxy or a remainder of an ester or amide group.

The compound of the formula [XV] is prepared by a reaction of the compound of the formula [VI] with the compound of the formula [XIV] in a presence of base. If the compound of the formula [XV] has a protected hydroxy group, the protevtive group is removed by an usual method to give the compound of the formula [XVI]. The compound of the formula [XVI] is reacted with trimethylsilyl halide and followed by a reaction with trialkyl phosphite to give the compound of the formula [XVII] of this invention.

In another way, the compound of of the formula [XVII] of this invention can be prepared by a reaction of the compound of the formula [VIII] with the compound of the formula [XVIII] in a presence of base.

The compound of the formula [XV] or [XVI] is also a novel compound which is especially useful as a synthetic intermediate to introduce a phosphono group into $R^4$.

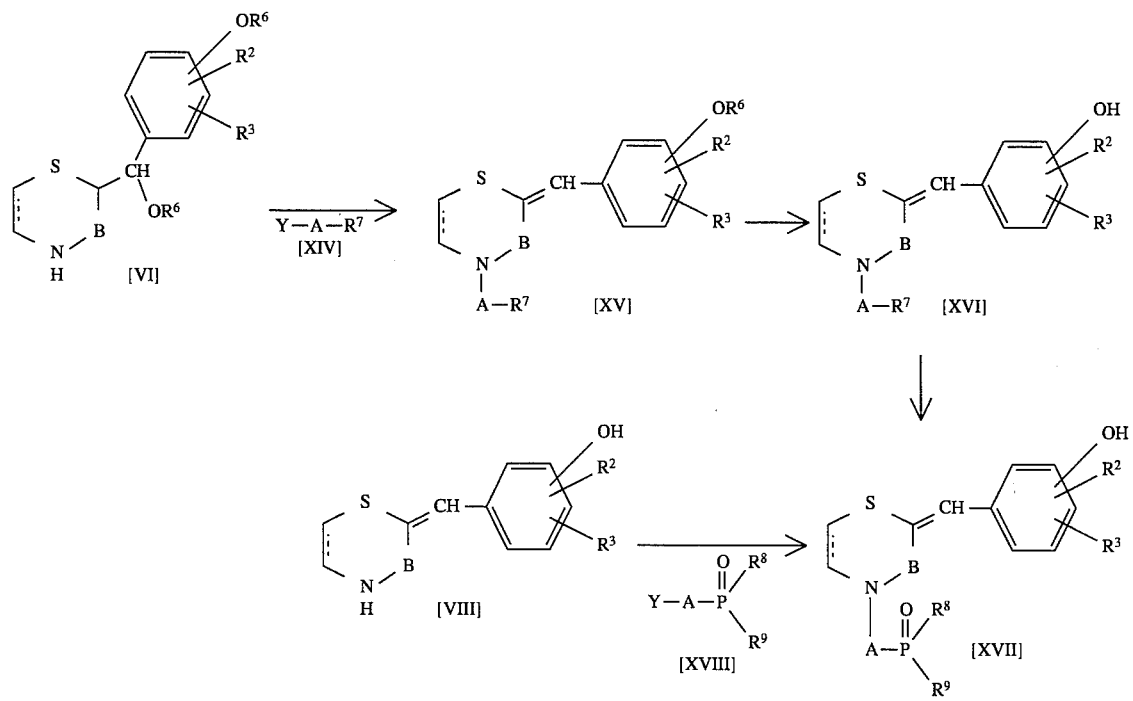

4) Synthesis of a compound wherein $R^4$ is represented by sulfonyl which can be converted into ester or amide.

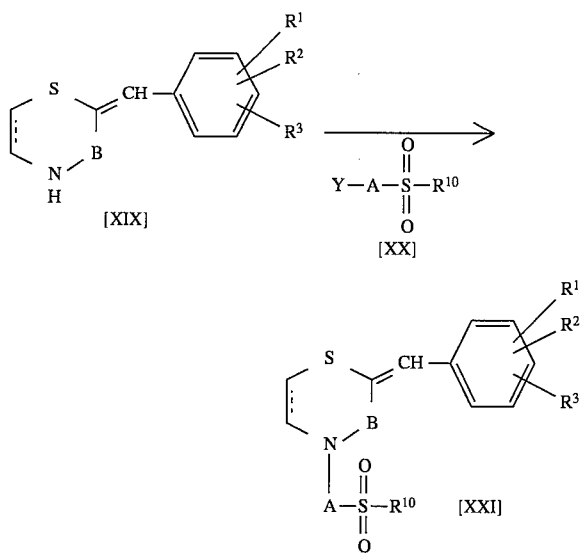

wherein $R^{10}$ is hydroxy, or a reminder of an ester or amide group.

The compound of the formula [XXI] of this invention is prepared by a reaction of the compound of the formula [XIX] with the compound of the formula [XX].

The compound of this invention wherein B is represented by C=S can be prepared by a treatment of the compound wherein B is represented by C=O with Lawesson's agent.

The compound of this invention wherein B is represented by $CH_2$ can be prepared by a reduction of the compound wherein B is represented by C=O with a reducing agent such as lithium aluminium halide/aluminium chloride.

A hydroxy group substituted on the phenyl ring of the benzylidene group may be protected by any of the above-mentioned protective groups by the usual method before or after the above-mentioned synthetic process, and the protective group can be removed by any usual method.

A carboxy, phosphono [-p (=O) $(OH)_2$] or sulfonyl group substituted at the 4th-position of 1,4-thiazine or thiomorpholine ring can be converted into ester or amide before or after the above-mentioned synthetic process by any usual method.

On the other hand, an ester or amide can be hydrolyzed to a carboxy, phosphono or sulfonyl group by any usual method.

The compounds prepared by the above methods can be converted into their salts as mentioned before by any usual method.

The compounds or intermediates of this invention may have stereoisomers or optical isomers, and these isomers are also included in this invention. For example, the compounds or intermediates of this invention may have Z-form or E-form because of the existence of benzylidene group, and these forms are included in this invention.

Hydrates of the compounds or intermediates of this invention are also included in this invention.

A compound which has a suppressive effect on lipid peroxide formation in combination with a protein stabilizing effect can be presumed to be especially useful for treatment of cataracts. A compound having both of these effects, however, has not been studied and development of such a compound is desirable.

Based on the information that 3-oxo-1,4-benzothiazine derivatives having benzylidene substituent at the 2nd-position have suppressive effect on lipid peroxide formation (Japanese Unexamined Patent Publication No. 287077/1989), the inventors focused attention on changing the ring system of 1,4-benzothiazine to 1,4-thiazine or thiomorpholine and started a study to solve the above-mentioned problem.

First, the inventors considered the information that toluene derivatives, in which hydroxy and tert.-butyl groups substituted, have anti-oxidizing effect. An anti-oxidizing agent exhibits a suppressive effect on lipid peroxide formation. Accordingly the inventors studied how substituents effect a suppressive effect on lipid peroxide formation, by introducing various kinds of substituents such as alkyl and hydroxy into the phenyl ring of a benzylidene group. As the result of the study, it was found that compounds having an excellent suppressive effect on lipid peroxide formation could be obtained by introducing hydroxy and lower alkyl groups into the phenyl ring of a benzylidene group.

Accordingly, the inventors fixed the main chemical structure of the compound of this invention to 1,4-thiazine or thiomorpholine having a benzylidene group at the 2nd-position, where the phenyl ring of the benzylidene group was further substituted by hydroxy and lower alkyl groups.

Second, the inventors synthesized novel compounds having various kinds of substituents at the 4th- position and carried out investigations to find a compound having a protein stabilizing effect. As the result of the investigations, the inventors found that a compound having an alkyl substituent, which was further substituted by an acidic moiety, that is carboxy, tetrazolyl, phosphono or sulfonyl, on nitrogen atom, namly the 4th-position of 1,4-thiazine or thiomorpholine, exhibited a protein stabilizing effect.

From these studies, the inventors found that 1,4-thiazine or thiomorpholine compounds, wherein the 4th-position was substituted by an alkyl group having an acidic moiety, that is, carboxy, tetrazolyl, phosphono or sulfonyl, and wherein the phenyl ring of the benzylidene group was further substituted by hydroxy and lower alkyl groups, showed an excellent suppressive effect on lipid peroxide formation in combination with a protein stabilizing effect. That is to say, the fundamental components of a compound according to this invention are (i) the 4th-position of 1,4-thiazine or thiomorpholine is substituted by an alkyl group having an acidic moiety, that is, carboxy, tetrazolyl, phosphono or sulfonyl, (ii) the 2nd-position is substituted by a benzylidene group, and (iii) the phenyl ring of the benzylidene group is further substituted by at least one hydroxy group and one lower alkyl group.

In the case of a medicament, conversion of the carboxy group, phosphono group or sulfonyl group into an ester or amide, or protection of the hydroxy group by a suitable protective group is generally applied to make pro-drugs in order to enhance the absorption or improve the duration of the medicament in the living body, or to make a compound stable. Furthermore, such techniques are generally used for manufacturing drugs. In other words, such a derived compound is generally used as a synthetic intermediate. Therefore in this invention, hydroxy groups may be protected by the widely used protective group for hydroxy, and carboxy groups, phosphono groups or sulfonyl groups may be converted into esters or amides.

The characteristic structure of the compound of this invention is that explained above, but a preferable example of the component is explained as follows.

$R^1$: Hydroxy is the best group. When the hydroxy group is pretected, lower alkanoyloxy, lower alkoxymethyloxy or benzoyloxy is preferable, lower alkanoyloxy or benzoyloxy is more preferable, and lower alkanoyloxy exemplified by acetyloxy is the most preferable.

R²: Methyl, isopropyl or tert.-butyl is preferable, and isopropyl or tert.-butyl is more preferable.

R³: Hydrogen, lower alkyl which may be substituted by amino or lower alkyl amino, lower alkoxy, hydroxy or tetrahydropyranyloxy is preferable, hydrogen, lower alkyl or lower alkoxy is more preferable, and lower alkyl, especially isopropyl or tert.-butyl, is the most preferable.

R⁴: Carboxy, tetrazolyl or phosphono is preferable. When the carboxy or phosphono group is converted into an ester or amide, lower alkylester such as methyl ester or ethyl ester is preferable, and amide with ammonia or lower alkylamine is preferable.

B: C=O is preferable.

A: Straight or branched alkylene containing 1 to 6 carbon atoms is preferable. Methylene or ethylene is more preferable.

Furthermore, a preferable example of the substituents on the phenyl ring of the benzylidene group is explained as follows.

A hydroxy group substitutes at the 4th-position, more preferably, lower alkyl group(s) substitute(s) at least one vicinal position of a hydroxy substituent. That is to say, it is preferable that lower alkyl group(s) substitute(s) at the 3rd-position or at both the 3rd- and 5th-positions.

In order to examine the effect of the compound of this invention, initially, an experiment to examine protein stabilizing effect was performed using bovine serum albumin. Details are shown in the article of Pharmacological Test described later in this specification. The inventors found that the compound of this invention had an excellent protein stabilizing effect.

Secondarily, in order to examine the suppressive effect on lipid peroxide formation of the compounds of this invention, an experiment was performed using microsomes of rat liver. As the result of the experiment, it was found that the compound of this invention had an excellent suppressive effect on lipid peroxide formation.

From the results of the above pharmacological tests, it was found that the compounds of this invention had a suppressive effect on lipid peroxide formation in combination with a protein stabilizing effect, and was useful for the treatment of cataract.

In addition, it is also reported that a chemical substance which has a suppressive effect on lipid peroxide formation or a protein stabilizing effect is applicable to an anti-inflammatory (Lancet, 1, 169 (1965), Biochem. Biophys. Acta., 489, 163 (1977)). Therefore it is expected that the compound of this invention is also useful as an anti-inflammatory.

Furthermore, an experiment was carried out according to the report of Kato et al. (Chem. Pharm. Bull., 33, (1) 74–83 (1985)), and it was also found that the compounds of this invention had an aldose reductase inhibiting effect. This result further supports the conclusion that the compounds of this invention are excellent therapeutic agents for cataract treatment and they are also expected to be useful for treatment of diabetic complications.

The compounds of this invention can be administered orally or parenterally. Examples of dosage forms are tablet, capsule, granule, powder, injection, ophthalmics, etc. The preparations can be prepared by the usual methods. For example, oral preparations such as a tablet, a capsule, a soft capsule and granules can be produced, if necessary, by adding diluents such as lactose, starch, crystalline cellulose or vegetable oil; lubricants such as magnesium stearate or talc; binders such as hydroxypropylcellulose or polyvinylpyrrolidone; a disintegrator such as carboxymethylcellulose calcium, or a coating agent such as hydroxypropylmethylcellulose. Ophthalmics can be prepared by adding a tonicity agent such as sodium chloride; a buffer such as sodium phosphate; a solubilizer such as polysorbate 80, or preservatives such as benzalkonium chloride.

The dosage is adjusted depending on symptoms, age, dosage form, etc., but in the case of oral preparations, the usual daily dosage is 1 to 5000 mg, preferably 1 to 1000 mg, which can be given in one or a few divided doses. In the case of ophthalmics, the dosage is 0.001 to 10%, preferably 0.01 to 5%, and one to several drops can be instilled per day.

Examples of preparations and formulations of the compounds of this invention are shown below. These examples do not limit the scope of this invention, but are intended to make this invention more clearly understandable.

EXAMPLE

1. REFERENCE EXAMPLE

Reference Example 1

2-(3,5-di-tert.-butyl-α,4-dihydroxybenzyl)-1,4-thiazine-3-one (reference compound 1-1)

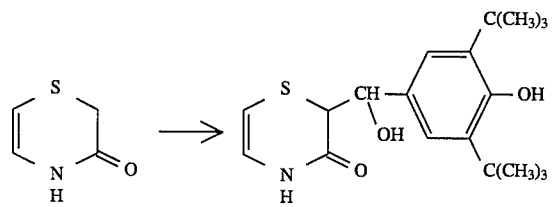

To a solution of diisopropylamine (24.3 ml) in tetrahydrofuran (120 ml), n-butyllithium dissolved in n-hexane( 1.6M, 95 ml), was added dropwise under a nitrogen atmosphere at −70° C. The mixture was stirred for 1 hour at −70° C. To the mixture, 1,4-thiazine-3-one (5.0 g) dissolved in tetrahydrofuran (20 ml) was added. After stirring for one hour at the same temperature, 3,5-di-tert.-butyl-4-hydroxybenzaldehyde (10.2 g) dissolved in a mixture of tetrahydrofuran (20 ml) and hexamethylphosphoric triamide (100 ml) was added dropwise to the mixture. The mixture was stirred for 2 hours at −70° C. Dilute hydrochloric acid was added to the mixture, and the whole was extracted with ethyl acetate. The organic layer was washed with saturated sodium chloride solution, dried over anhydrous sodium sulfate and concentrated in vacuo. The oily residue was purified by silica gel column chromatography to give 7.6 g (50%) of the titled compound.

mp 216.7°–218.7° C.

IR (KBr, cm⁻¹) 3637, 3347, 2956, 1655, 1623, 1442, 1400, 1372, 1331, 1308, 1237, 1214, 1187

The following compounds can be prepared by a method similar to Reference Example 1.

2-(α,4-dihydroxy-3,5-diisopropylbenzyl)-1,4-thiazine-3-one (reference compound 1-2)

mp 166.2°–167.8° C.

IR (KBr, cm⁻¹) 3598, 3318, 3077, 2963, 2870, 1651, 1447, 1376, 1309, 1278, 1260, 1189, 1176, 1148, 1125

2-(3-tert.-butyl-α,4-dihydroxybenzyl)-1,4-thiazine-3-one (reference compound 1-3)

2-(α,4-dihydroxy-3,5-dimethylbenzyl)-1,4-thiazine-3-one (reference compound 1-4)

2-(α,4-dihydroxy-3-methoxy-5-methylbenzyl)-1,4-thiazine-3-one (reference compound 1-5)

2-(5-tert.-butyl-α,4-dihydroxy-3-dimethylaminomethylbenzyl)- 1,4-thiazine-3-one (reference compound 1-6)

2-[5-tert.-butyl-α,4-dihydroxy-3-[1,1-dimethyl-2-(tetrahydropyran- 2-yloxy)ethyl]benzyl]-1,4-thiazine-3-one (reference compound 1-7)

2-(3,5-di-tert.-butyl-α-hydroxy-4-methoxymethoxybenzyl)-1,4-thiazine- 3-one (reference compound No.1-8)

Reference Example 2

2-(3,5-di-tert.-butyl-α,4-dihydroxybenzyl)thiomorpholine-3-one (reference compound No.2-1)

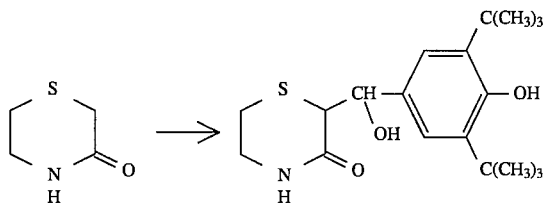

To a solution of diisopropylamine (71.8 ml) in tetrahydrofuran (400 ml), n-butyllithium dissolved in n-hexane (1.6M, 320 ml), was added dropwise under a nitrogen atmosphere at −70° C. The mixture was stirred for 50 minutes at −70° C. To the mixture, thiomorpholine-3-one (20.0 g) dissolved in tetrahydrofuran (200 ml) was added. After one hour stirring at the same temperature, 3,5-di-tert.-butyl-4-hydroxybenzaldehyde (40.0 g) dissolved in a mixture of tetrahydrofuran (50 ml) and hexamethylphosphoric triamide (200 ml) was added dropwise to the mixture. The mixture was stirred for 2 hours at −70° C. Dilute hydrochloric acid was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 24.17 g (40%) of the titled compound of erythro form and 2.84 g (5%) of the titled compound of threo form.

erythro form:

mp 178.5°–179.8° C.

IR (KBr, cm$^{-1}$) 3638, 3306, 3107, 2955, 1659, 1480, 1439, 1400, 1363, 1319, 1271 threo form:

mp 167.7°–168.3° C.

IR (KBr, cm$^{-1}$) 3640, 3558, 3344, 2952, 2917, 2883, 1670, 1651, 1486, 1468, 1435, 1412, 1390, 1374

The following compounds can be prepared by a method similar to Reference Example 2.

2-(α,4-dihydroxy-3,5-diisopropylbenzyl)thiomorpholine-3-one (reference compound No.2-2)

erythro form:

mp 85.5°–86.7° C.

IR (KBr, cm$^{-1}$) 3304, 2962, 2869, 1657, 1470, 1362, 1342, 1284, 1200, 1153, 1123, 1032, 936 threo form:

IR (KBr, cm$^{-1}$) 3348, 2961, 1651, 1471, 1286, 1202, 1153, 1121, 936, 881, 816, 755, 665

2-(3-tert.-butyl-α,4-dihydroxybenzyl)thiomorpholine-3-one (reference compound No.2-3)

erythro form:

mp 163.5°–165.8° C. (dec.)

IR (KBr, cm$^{-1}$) 3387, 3188, 2935, 1647, 1382, 1206, 1010, 834, 619 threo form:

IR (KBr, cm$^{-1}$) 3306, 2954, 1652, 1483, 1424, 1343, 1260, 1202, 1085, 820

2-(α,4-dihydroxy-3,5-dimethylbenzyl)thiomorpholine-3-one (reference compound No.2-4)

erythro form:

mp 177.7°–179.1° C.

IR (KBr, cm$^{-1}$) 3358, 3011, 2914, 1626, 1485, 1442, 1382, 1345, 1293, 1218, 1150, 1111, 1046, 1023, 997, 964, 954 threo form:

mp 178.7°–180.0° C.

IR (KBr, cm$^{-1}$) 3365, 2918, 2875, 1634, 1605, 1480, 1448, 1384, 1345, 1303, 1275, 1186, 1144, 1109, 1076, 1015

2-(α,4-dihydroxy-3-methoxy-5-methylbenzyl)thiomorpholine-3-one (reference compound No.2-5)

erythro form:

IR (KBr, cm$^{-1}$) 3494, 3360, 2986, 1670, 1644, 1613, 1466, 1302, 1221, 1090, 852, 677 threo form:

mp 173.0°–174.8° C. (dec.)

IR (KBr, cm$^{-1}$) 3375, 3184, 3042, 2917, 1654, 1645, 1487, 1429, 1319, 1075, 828, 704

2-(5-tert.-butyl-α, 4-dihydroxy-3-dimethylaminomethylbenzyl)thiomorpholine- 3-one (reference compound No. 2-6)

2-[5-tert.-butyl-α, 4-dihydroxy-3-[1, 1-dimethyl-2-(tetrahydropyran- 2-yloxy)ethyl]benzyl]thiomorpholine-3-one (reference compound 2- 7)

2- (3, 5-di-tert.-butyl-α-hydroxy-4-methoxymethoxybenzyl)thiomorpholine- 3-one (reference compound No. 2-8)

Reference Example 3

2-(3,5-di-tert.-butyl-4-hydroxybenzylidene)-1,4-thiazine-3-one (reference compound 3-1)

To a solution of 2-(3,5-di-tert.-butyl-α,4-dihydroxybenzyl)- 1,4-thiazine-3-one (reference compound No.1-1, 0.20 g) in a mixture of methylenechloride (5 ml) and tetrahydrofuran (5 ml), triethylamine (0.24 ml) and methanesulfonyl chloride (0.07 ml) were added under ice cooling. The mixture was stirred for 15 minutes under ice cooling. Dilute hydrochloric acid was added to the mixture, and the whole was extracted with chloroform. The organic layer was washed with saturated sodium chloride solution, dried over anhydrous sodium sulfate and concentrated in vacuo. The oily residue was purified by silica gel column chromatography to give 0.19 g (100%) of the titled compound.

mp 208.7°–210.6° C.

IR (KBr, cm$^{-1}$) 3630, 3374, 3195, 3068, 2962, 1658, 1625, 1574, 1481, 1434, 1418, 1381, 1331

The following compounds can be prepared by a method similar to Reference Example 3 using a reference compound 1-7 or 1-8 for a starting material.

2-[5-tert.-butyl-3-[1,1-dimethyl-2-(tetrahydropyran-2-yloxy)ethyl]-4-hydroxybenzylidene]-1,4-thiazine-3-one (reference compound 3- 2)

2-(3,5-di-tert.-butyl-4-methoxymethoxybenzylidene)-1,4-thiazine- 3-one (reference compound 3-3)

Reference Example 4

2-(3,5-di-tert.-butyl-4-hydroxybenzylidene)thiomorpholine-3-one (reference compound 4-1)

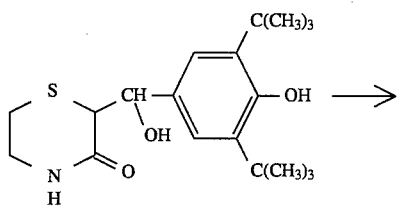

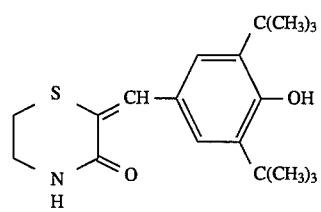

To a solution of the erythro form of 2-(3,5-di-tert.-butyl-α, 4-dihydroxybenzyl)thiomorpholine-3-one(reference compound2-1, 10.0 g) in a mixture of methylene chloride (40 ml) and tetrahydrofuran (40 ml), triethylamine (11.9 ml) and methanesulfonyl chloride (3.3 ml) were added under ice cooling. The mixture was stirred for 1 hour under ice cooling. Dilute hydrochloric acid was added to the mixture, and the whole was extracted with chloroform. The organic layer was washed with saturated sodium chloride solution, dried over anhydrous magnesium sulfate and concentrated in vacuo. The oily residue was purified by silica gel column chromatography to give 8.13 g (87%) of the titled compound.

mp 192°–196° C.

IR (KBr, cm$^{-1}$) 3616, 3168, 2960, 1640, 1580, 1472, 1418, 1390, 1362, 1339, 1290, 1262, 1197, 1120

The following compounds can be prepared by a method similar to Reference Example 4 using a reference compound 2-7 or 2-8 for a starting material.

2-[5-tert.-butyl-3-[1,1-dimethyl-2-(tetrahydropyran-2-yloxy)ethyl]-4-hydroxybenzylidene]thiomorpholine-3-one (reference compound 4-2)

2-(3 , 5-di-tert.-butyl-4-methoxymethoxybenzylidene)thiomorpholine- 3-one (reference compound 4-3)

Reference Example 5

2-(α,4-diacetoxy-3,5-diisopropylbenzyl)-1,4-thiazine-3-one (reference compound No.5-1)

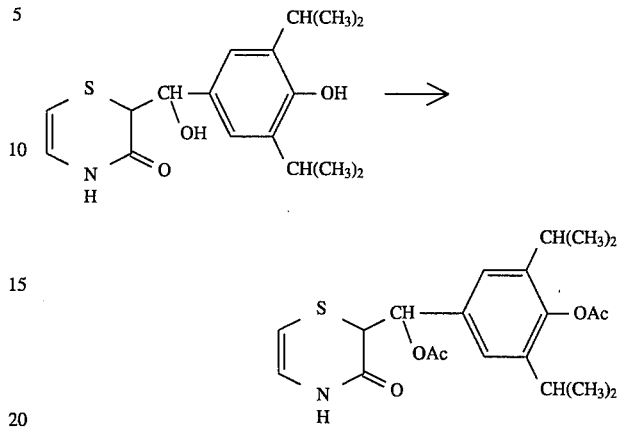

To a solution of 2-(α,4-dihydroxy-3,5-diisopropylbenzyl)- 1,4-thiazine-3-one (reference compound No.1-2, 3.43 g) in pyridine (17.3 ml), acetic anhydride (10.1 ml) was added under a nitrogen atmosphere. The mixture was stirred for 24 hours at room temperature. 1N hydrochloric acid was added to the mixture, and the whole was extracted with ethyl acetate. The organic layer was washed with 1N sodium hydroxide solution and saturated sodium chloride solution, dried over anhydrous magnesium sulfate and concentrated in vacuo. The oily residue was purified by silica gel column chromatography to give 3.26 g (75%) of the titled compound.

mp 206.8°–208.4° C.

IR (KBr, cm$^{-1}$) 3359, 3084, 3030, 2965, 2872, 1757, 1725, 1672, 1631, 1457, 1372, 1335, 1319, 1306, 1244, 1213

The following compounds can be prepared by a method similar to Reference Example 5 using a reference compound 1-2- 1-6 for a starting material.

2-(α,4-dibenzoyloxy-3,5-diisopropylbenzyl)-1,4-thiazine-3-one (reference compound No.5-2)

2-(3-tert.-butyl-α,4-diacetoxybenzyl)-1,4-thiazine-3-one (reference compound No. 5-3)

2-(α,4-diacetoxy-3,5-dimethylbenzyl)-1,4-thiazine-3-one (reference compound No. 5-4)

2-(α,4-diacetoxy-5-methoxy-3-methylbenzyl)-1,4-thiazine-3-one (reference compound No.5-5)

2-(5-tert.-butyl-α,4-diacetoxy-3-dimethylaminomethylbenzyl)-1,4-thiazine- 3-one (reference compound No.5-6)

Reference Example 6

2-(α,4-diacetoxy-3,5-diisopropylbenzyl)thiomorpholine-3-one (reference compound No.6-1)

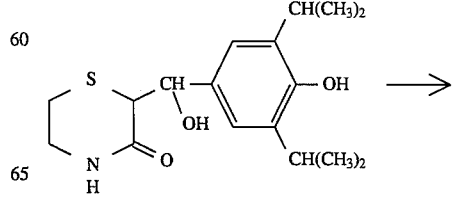

15
-continued

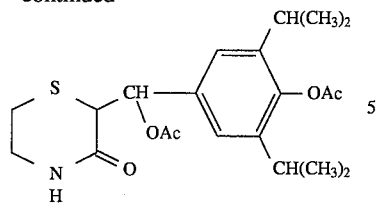

To a suspension of 2-(α,4-dihydroxy-3,5-diisopropylbenzyl)thiomorpholine- 3-one (reference compound No.2-2, 2.00 g) in methylene chloride (20 ml), pyridine (15.00 ml) was added and the mixture was stirred for 8 hours at 40° C. The mixture was poured into 1N hydrochloric acid under ice cooling, and the whole was extracted with methylene chloride. The organic layer was washed with saturated aqueous sodium hydrogen carbonate soluton and saturated sodium chloride solution, dried over anhydrous magnesium sulfate and concentrated in vacuo to give 1.99 g (79%) of the titled compound.

mp 159.3°–160.1° C.

IR (KBr, cm$^{-1}$) 3180, 3043, 2961, 1768, 1749, 1664, 1488, 1471, 1429, 1368, 1346, 1302, 1277, 1233, 1213

The following compounds can be prepared by a method similar to Reference Example 6 using a reference compound 2-2- 2-6 for a starting material.

2-(α,4-dibenzoyloxy-3,5-diisopropylbenzyl)thiomorpholine-3-one (reference compound No.6-2)

2-(3-tert.-butyl-α,4-diacetoxybenzyl )thiomorpholine-3-one (reference compound No. 6-3)

mp 170.5°–174° C. (dec.)

IR (KBr, cm$^{-1}$) 3204, 2980, 1751, 1728, 1652, 1489, 1370, 1250, 1214, 1028, 828

2-(α,4-diacetoxy-3,5-dimethylbenzyl)thiomorpholine-3-one (reference compound No.6-4)

mp 175.6°–184.2° C.

IR (KBr, cm$^{-1}$) 3204, 3087, 2932, 2888, 1753, 1680, 1611, 1484, 1411

2-(α,4-diacetoxy-5-methoxy-3-methylbenzyl)thiomorpholine-3-one (reference compound No.6-5)

mp 144.5°–147.6° C. (dec.)

IR (KBr, cm$^{-1}$) 3375, 3184, 3042, 2917, 1654, 1645, 1487, 1429, 1319, 1075, 828, 704

2-(5-tert.-butyl-α,4-diacetoxy-3-dimethylaminomethylbenzyl)thiomorpholine- 3-one (reference Compound No. 6-6)

Reference Example 7

2-(3,5-di-tert.-butyl-4-hydroxybenzylidene)thiomorpholine (reference compound No.7-1)

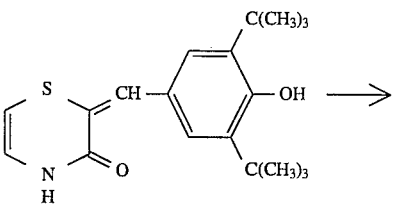

16
-continued

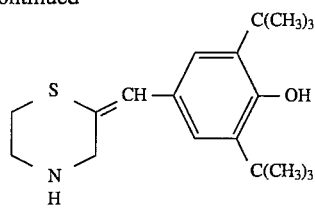

To a suspension of lithium aluminum hydride (0.29 g) in diethyl ether (8 ml), aluminum chloride (0.34 g) was added under a nitrogen atmosphere. The mixture was stirred for 15 minutes at room temperature. To the mixture, 2-(3,5-di-tert.-butyl-4-hydroxybenzylidene)- 1,4-thiazine-3-one (reference compound No.3- 1, 0.50 g) dissolved in a mixture of diethyl ether (2 ml) and tetrahydrofuran (6 ml) was added. The mixture was stirred for 30 minutes at room temperature. Water was added to the mixture, and the whole was extracted with ethyl acetate. The organic layer was washed with saturated sodium chloride solution, dried over anhydrous sodium sulfate and concentrated in vacuo. The oily residue was purified by silica gel column chromatography to give 0.26 g (54%) of the titled compound.

mp 150.5°–151.7° C.

IR (KBr, cm$^{-1}$) 3315, 2947, 1614, 1596, 1570, 1483, 1430, 1397, 1372, 1352, 1340, 1319, 1290, 1270, 1235

2. EXAMPLE

Example 1

2-(3,5-di-tert.-butyl-4-methoxymethoxybenzylidene)-4-methoxymethylthiomorpholine- 3-one (compound No. 1-1)

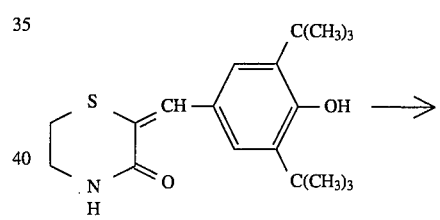

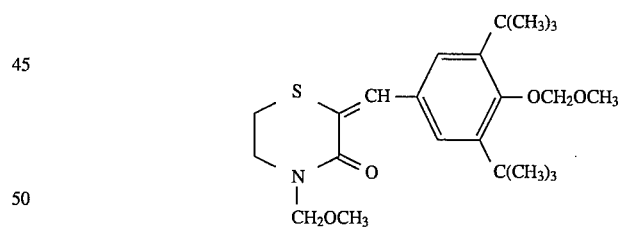

To a suspension of sodium hydride (60% suspension in paraffin liquid, 0.96 g) in tetrahydrofuran (20 ml), 2-(3,5-di-tert.-butyl- 4-hydroxybenzylidene)thiomorpholine-3-one (reference compound No.4-1, 4.00 g) dissolved in tetrahydrofuran (50 ml) was added dropwise under a nitrogen atmosphere and ice-salt cooling. The mixture was stirred for 30 minutes at room temperature. To the mixture, methoxymethyl chloride (1.82 ml) dissolved in tetrahydrofuran (10 ml) was added and the mixture was stirred for 3 hours. Water was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 2.33 g (46%) of the titled compound.

IR (Film, cm$^{-1}$) 2957, 1644, 1574, 1469, 1430, 1390, 1189, 1166, 1111, 1081, 964

The following compound can be prepared by a method similar to Example 1 using a reference compound 4-2 for a starting material.

2-[5-tert.-butyl-3-[1,1-dimethyl-2-(tetrahydropyran-2-yloxy)ethyl]-4-methoxymethoxybenzylidene]-4-methoxymethylthiomorpholine- 3-one (compound No. 1- 2)

Example 2

2-(3,5-di-tert.-butyl-4-methoxymethoxybenzylidene)-4-methoxymethyl- 1,4-thiazine-3-one (compound No. 2-1)

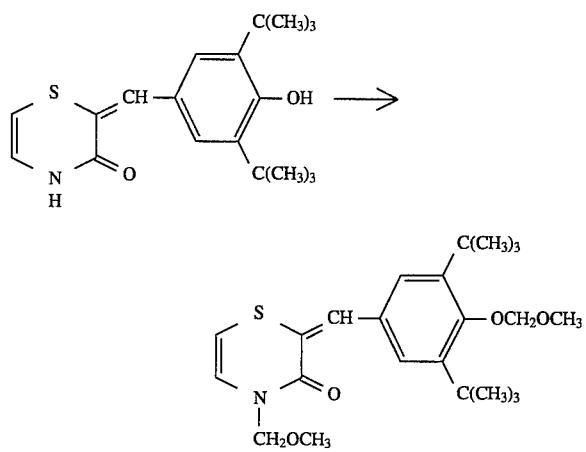

To a suspension of sodium hydride (60% suspension in paraffin liquid, 0.06 g) in tetrahydrofuran (2 ml), 2-(3,5-di-tert.-butyl- 4-hydroxybenzylidene)-1,4-thiazine-3-one (reference compound No.3-1, 0.23 g) dissolved in tetrahydrofuran (5 ml) was added dropwise under a nitrogen atmosphere and ice-salt cooling. The mixture was stirred for 10 minutes at room temperature. To the mixture, methoxymethyl chloride (0.1 ml) dissolved in tetrahydrofuran (1 ml) was added and the mixture was stirred for 2 hours. Water was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give the titled compound.

The following compound can be prepared by a method similar to Example 2 using a reference compound 3-2 for a starting material.

2-[5-tert.-butyl-3-[1,1-dimethyl-2-(tetrahydropyran-2-yloxy)ethyl]-4-methoxymethoxybenzylidene]-4-methoxymethyl-1,4-thiazine- 3-one (compound No. 2- 2)

Example 3

2-(4-acetoxy-3,5-diisopropylbenzylidene)-4-methoxymethylthiomorpholine- 3-one (compound No. 3- 1)

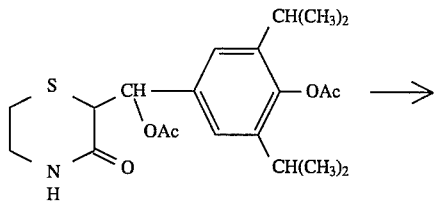

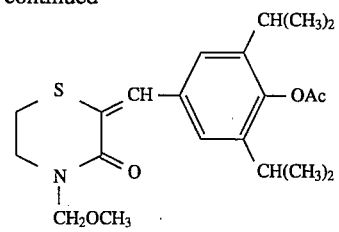

To a suspension of sodium hydride (60% suspension in paraffin liquid, 0.14 g) in tetrahydrofuran (3 ml), 2-(α,4-diacetoxy- 3,5-diisopropylbenzyl)thiomorpholine-3-one (reference compound No.6-1, 1.21 g) dissolved in tetrahydrofuran (8 ml) was added dropwise under a nitrogen atmosphere and ice-salt cooling. The mixture was stirred for 30 minutes at room temperature. To the mixture, methoxymethyl chloride (0.3 ml) dissolved in tetrahydrofuran (2 ml) was added and the mixture was stirred for 3 hours. Water was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give the titled compound.

The following compounds can be prepared by a method similar to Example 3 using a reference compound 6-2- 6-6 for a starting material.

2-(4-benzoyloxy-3 , 5-diisopropylbenzylidene)-4-methoxymethylthiomorpholine- 3-one (compound No. 3-2)

2-(4-acetoxy-3-tert.-butylbenzylidene)-4-methoxymethylthiomorpholine- 3-one (compound No. 3-3)

2-(4-acetoxy-3,5-dimethylbenzylidene)-4-methoxymethylthiomorpholine- 3-one (compound No. 3-4)

2-(4-acetoxy- 5-methoxy-3-methylbenzylidene)-4-methoxymethylthiomorpholine- 3-one (compound No. 3-5)

2-(4-acetoxy-5-tert.-butyl-3-dimethylaminomethylbenzylidene)-4-methoxymethylthiomorpholine- 3-one (compound No. 3-6)

Example 4

2-(4-acetoxy-3,5-diisopropylbenzylidene)-4-methoxymethyl-1,4-thiazine- 3-one (compound No. 4-1)

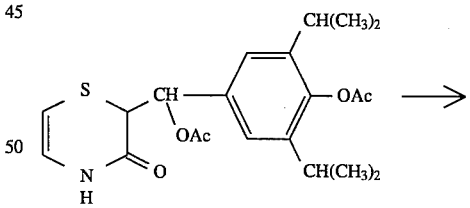

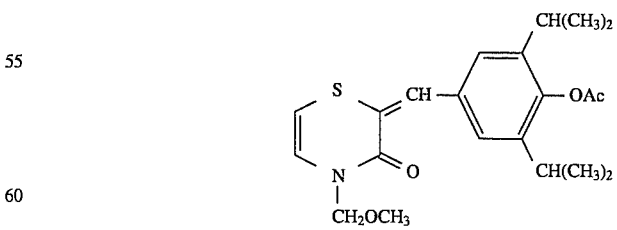

To a suspension of sodium hydride (60% suspension in paraffin liquid, 0.16 g) in tetrahydrofuran (3 ml), 2-(α,4-diacetoxy- 3,5-diisopropylbenzyl)-1,4-thiazine-3-one (reference compound No.5-1, 1.35 g) dissolved in tetrahydrofuran (8 ml) was added dropwise under a nitrogen atmosphere and ice-salt cooling. The mixture was stirred for 15 minutes at room temperature. To the mixture, methoxymethyl chloride (0.3 ml) dissolved in tetrahydrofuran (2 ml) was added and the mixture was stirred for 3 hours. Water was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give the titled compound.

The following compounds can be prepared by a method similar to Example 4 using a reference compound 5-2- 5-6 for a starting material.

2-(4-benzoyloxy-3,5-diisopropylbenzylidene)-4-methoxymethyl-1,4-thiazine- 3-one (compound No. 4-2)

2-(4-acetoxy-3-tert.-butylbenzylidene)-4-methoxymethyl-1,4-thiazine- 3-one (compound No. 4-3)

2-(4-acetoxy-3,5-dimethylbenzylidene)-4-methoxymethyl-1,4-thiazine- 3-one (compound No. 4-4)

2-(4-acetoxy-5-methoxy-3-methylbenzylidene)-4-methoxymethyl-1,4-thiazine- 3-one (compound No. 4-5)

2-(4-acetoxy-5-tert.-butyl-3-dimethylaminomethylbenzylidene)-4-methoxymethyl- 1,4-thiazine-3-one (compound No. 4-6)

Example 5

2-(3 , 5-diisopropyl-4-hydroxybenzylidene)-4-methoxymethylthiomorpholine- 3-one (compound No. 5-1)

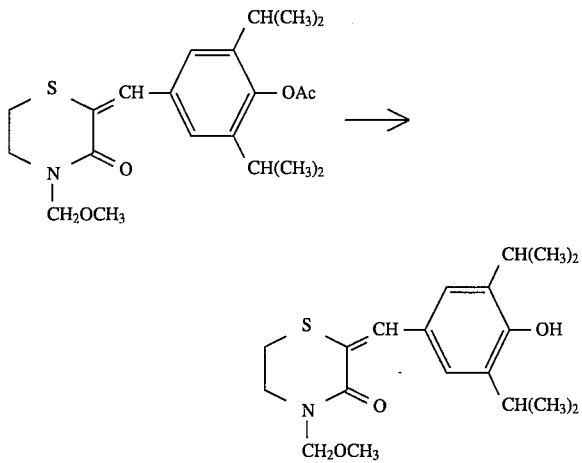

To a solution of 2-(4-acetoxy-3,5-diisopropylbenzylidene)- 4-methoxymethylthiomorpholine-3-one (compound No.3-1, 0.83 g) in tetrahydrofuran (18 ml), lithium hydroxide monohydrate (0.89 g) dissolved in water(14 ml) was added dropwise under ice cooling. The mixture was stirred for 1 hour. Dilute hydrochloric acid was added to the mixture to acidify it, and the whole was extracted with ethyl acetate. The organic layer was washed with saturated sodium chloride solution, dried over anhydrous magnesium sulfate and concentrated in vacuo. The oily residue was purified by silica gel column chromatography to give the titled compound.

The following compounds can be prepared by a method similar to Example 5 using a compound 3-3-3-6 for a starting material.

2-(3-tert.-butyl-4-hydroxybenzylidene)-4-methoxymethylthiomorpholine- 3-one (compound No. 5-2)

2-(3 , 5-dimethyl-4-hydroxybenzylidene)-4-methoxymethylthiomorpholine- 3-one (compound No. 5-3)

2-(4-hydroxy-5-methoxy-3-methylbenzylidene)-4-methoxymethylthiomorpholine- 3-one (compound No. 5-4)

2-(5-tert.-butyl-3-dimethylaminomethyl-4-hydroxybenzylidene)-4-methoxymethylthiomorpholine- 3-one (compound No. 5-5)

Example 6

2-(3,5-diisopropyl-4-hydroxybenzylidene)-4-methoxymethyl-1,4-thiazine- 3-one (compound No. 6-1)

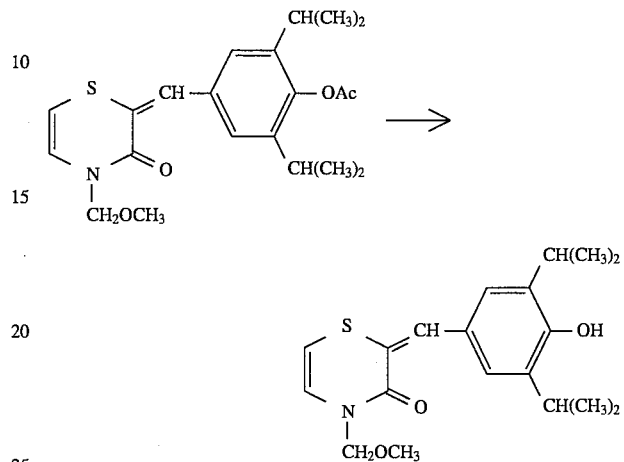

To a solution of 2-(4-acetoxy-3,5-diisopropylbenzylidene)- 4-methoxymethyl-1,4-thiazine-3-one (compound No.4-1, 0.42 g) in tetrahydrofuran (14 ml), lithium hydroxide monohydrate (0.45 g) dissolved in water(11 ml) was added dropwise under ice cooling. The mixture was stirred for 1 hour. Dilute hydrochloric acid was added to the mixture to acidify it, and the whole was extracted with ethyl acetate. The organic layer was washed with saturated sodium chloride solution, dried over anhydrous magnesium sulfate and concentrated in vacuo. The oily residue was purified by silica gel column chromatography to give the titled compound.

The following compounds can be prepared by a method similar to Example 6 using a compound 4-3-4-6 for a starting material.

2-(3-tert.-butyl-4-hydroxybenzylidene)-4-methoxymethyl-1,4-thiazine- 3-one (compound No. 6-2)

2-(3,5-dimethyl-4-hydroxybenzylidene)-4-methoxymethyl-1,4-thiazine- 3-one (compound No. 6-3)

2-(4-hydroxy-5-methoxy-3-methylbenzylidene)-4-methoxymethyl- 1,4-thiazine-3-one (compound No. 6-4)

2-(5-tert.-butyl-3-dimethylaminomethyl-4-hydroxybenzylidene)-4-methoxymethyl- 1,4-thiazine-3-one (compound No. 6-5)

Example 7

2-(3 , 5-di-tert.-butyl-4-hydroxybenzylidene)-4-phosphonomethylthiomorpholine- 3-one diethyl ester (compound No. 7-1)

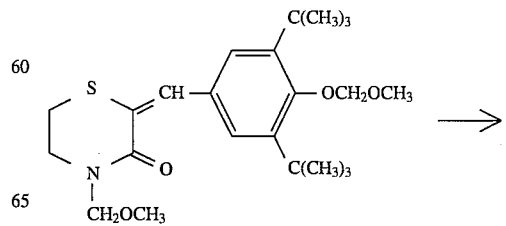

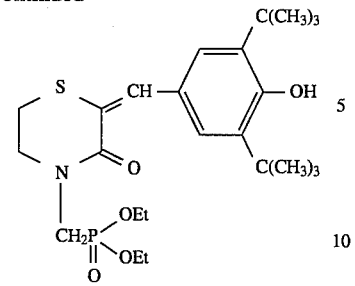

To a solution of 2-(3,5-di-tert.-butyl-4-methoxymethoxybenzylidene)- 4- methoxymethylthiomorpholine-3-one (compound No. 1-1, 2.33 g) in chloroform (55 ml), trimethylsilyliodide (1.97 g) was added dropwise under ice-salt cooling. After 15 minutes stirring, triethyl phosphite (5.4 ml) was added to the mixture. The mixture was stirred for 10 minutes. Water was added to the mixture, and the whole was extracted with chloroform. The organic layer was washed with saturated sodium chloride solution, dried over anhydrous magnesium sulfate and concentrated in vacuo. The oily residue was purified by silica gel column chromatography to give 1.40 g (56%) of the titled compound.

mp 159.3°–162.0° C.

IR (KBr, cm$^{-1}$) 3120, 2952, 1636, 1572, 1472, 1437, 1340, 1263, 1203, 1013

The following compounds can be prepared by a method similar to Example 7 using a compound 5-1, 5-2, 5-3 or 5-5 for a starting material.

4-phosphonomethyl-2-(3 , 5-diisopropyl-4-hydroxybenzylidene)thiomorpholine- 3-one diethyl ester (compound No. 7-2)

2-(3-tert.-butyl-4-hydroxybenzylidene)-4-phosphonomethylthiomorpholine- 3-one diethyl ester (compound No. 7-3)

4-phosphonomethyl-2-(3 , 5-dimethyl-4-hydroxybenzylidene)thiomorpholine- 3-one diethyl ester (compound No. 7-4)

2-(5-tert.-butyl-3-dimethylaminomethyl-4-hydroxybenzylidene)-4-phosphonomethylthiomorpholine- 3-one diethyl ester (compound No. 7-5)

Example 8

2-(3,5-di-tert.-butyl-4-hydroxybenzylidene)-4-(2-phosphonoethyl)- 1,4-thiazine-3-one diethyl ester (compound No. 8- 1)

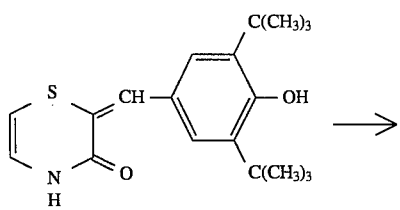

To a suspension of sodium hydride (60% suspension in paraffin liquid, 0.026 g) in tetrahydrofuran (1 ml), 2-(3,5-di-tert.-butyl- 4-hydroxybenzylidene)-1,4-thiazine-3-one (reference compound No. 3-1, 0.099 g) dissolved in tetrahydrofuran (1.4 ml) was added dropwise under a nitrogen atmosphere and ice-salt cooling. The mixture was stirred for 20 minutes at room temperature. To the mixture, diethyl 2-bromoethylphosphate (0.096 g) dissolved in tetrahydrofuran (1 ml) was added. The mixture was stirred for 4 hours at room temperature. Aqueous ammonium chloride solution was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 0.11 g (75%) of the titled compound.

IR (Film, cm$^{-1}$) 3440, 2958, 1737, 1644, 1568 1435, 1421 1393, 1359, 1248, 1027, 970

The following compounds can be prepared by a method similar to Example 8 using a reference compound 3-2 or 5-1-5-6 for a starting material.

2-[5-tert.-butyl-3-[1,1-dimethyl-2-(tetrahydropyran-2-yloxy)ethyl]-4-hydroxybenzylidene]-4-(2-phosphonoethyl)-1,4-thiazine- 3-one diethyl ester (compound No. 8-2)

2-(4-acetoxy-3,5-diisopropylbenzylidene)-4-(2-phosphonoethyl)- 1,4-thiazine-3-one diethyl ester (compound No. 8-3)

2-(4-benzoyloxy-3,5-diisopropylbenzylidene)-4-(2-phosphonoethyl)- 1,4-thiazine-3-one diethyl ester (compound No. 8- 4)

2-(4-acetoxy-3-tert.-butylbenzylidene)-4-(2-phosphonoethyl)-1,4-thiazine- 3-one diethyl ester (compound No. 8-5)

2-(4-acetoxy-3,5-dimethylbenzylidene)-4-(2-phosphonoethyl)-1,4-thiazine- 3-one diethyl ester (compound No. 8-6)

2-(4-acetoxy-5-methoxy-3-methylbenzylidene)-4-(2-phosphonoethyl)- 1,4-thiazine-3-one diethyl ester (compound No. 8- 7)

2-(4-acetoxy-5-tert.-butyl-3-dimethylaminomethylbenzylidene)-4-( 2-phosphonoethyl)-1,4-thiazine-3-one diethyl ester (compound No. 8-8)

2-(3 , 5-di-tert.-butyl-4-hydroxybenzylidene)-4-(7-phosphonoheptyl)- 1,4-thiazine-3-one diethyl ester (compound No. 8-9)

Example 9

2-(3,5-di-tert.-butyl-4-hydroxybenzylidene)-4-phosphonomethylthiomorpholine- 3-one (compound No. 9-1)

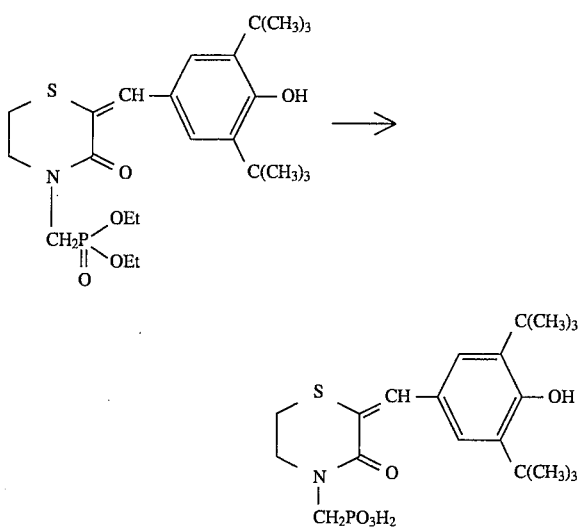

To a solution of 2-(3,5-di-tert.-butyl-4-hydroxybenzylidene)- 4-phosphonomethylthiomorpholine-3-one diethyl ester (compound No. 7-1, 1.00 g) in dioxane (38 ml), 5.8N hydrochloric aid (28 ml) was added and the mixture was stirred for 1 hour at room temperature. The mixture was poured into dilute hydrochloric acid and the whole was extracted with diethyl ether. The organic layer was washed with saturated sodium chloride solution, dried over anhydrous magnesium sulfate and concentrated in vacuo. The oily residue was purified by silica gel column chromatography to give 0.17 g (19.2%) of the titled compound.

IR (KBr, cm$^{-1}$) 3626, 2958, 1608, 1564, 1476, 1438, 1421, 1343, 1209, 1156, 1008, 754

The following compounds can be prepared by a method similar to Example 9 using a compound 7-2- 7-5 for a starting material.

2-(3 , 5-di-isopropyl-4-hydroxybenzylidene)-4-phosphonomethylthiomorpholine- 3-one (compound No. 9-2)

2-(3-tert.-butyl-4-hydroxybenzylidene)-4-phosphonomethylthiomorpholine- 3-one (compound No. 9-3)

2-(3 , 5-dimethyl-4-hydroxybenzylidene)-4-phosphonomethylthiomorpholine- 3-one (compound No. 9-4)

2-(5-tert.-butyl-3-dimethylaminomethyl-4-hydroxybenzylidene)-4-phosphonomethylthiomorpholine- 3-one (compound No. 9-5)

Example 10

4-cyanomethyl-2-(3,5-di-tert.-butyl-4-hydroxybenzylidene)-1,4-thiazine- 3-one (compound No. 10-1)

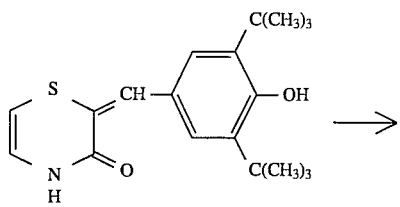

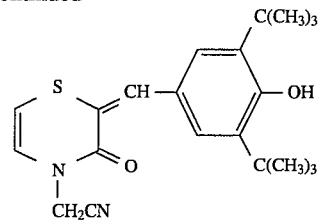

To a suspension of sodium hydride (60% suspension in paraffin liquid, 0.19 g) in tetrahydrofuran (5 ml), 2-(3,5-di-tert.-butyl- 4-hydroxybenzylidene)-1,4-thiazine-3-one (reference compound No. 3-1, 0.80 g) dissolved in tetrahydrofuran (15 ml) was added dropwise under a nitrogen atmosphere. The mixture was stirred for 20 minutes at room temperature. To the mixture, bromoacetonitrile (0.34 ml) was added and the mixture was stirred for 15 hours at room temperature. 1N hydrochloric acid was added to the mixture, and the whole was extracted with ethyl acetate. The organic layer was washed with saturated sodium chloride solution, dried over anhydrous sodium sulfate and concentrated in vacuo. The oily residue was purified by silica gel column chromatography to give 0.45 g (50%) of the titled compound.

mp 158.9°–160.5° C.

IR (KBr, cm$^{-1}$) 3625, 3082, 2956, 2365, 1636, 1582, 1557, 1438, 1420, 1386, 1362

The following compounds can be prepared by a method similar to Example 10 using a reference compound 3-1- 3-3 for a starting material.

4-(3-cyanopropyl)-2-(3,5-di-tert.-butyl-4-hydroxybenzylidene)- 1,4-thiazine-3-one (compound No. 10-2)

4-cyanomethyl-2-[5-tert.-butyl-3-[1,1-dimethyl-2-(tetrahydropyran- 2-yloxy)ethyl]-4-hydroxybenzylidene]-1,4-thiazine- 3-one (compound No. 10-3)

4-cyanomethyl-2-(3 , 5-di-tert.-butyl-4-methoxymethoxybenzylidene)- 1,4-thiazine-3-one (compound No. 10-4)

4-(7-cyanoheptyl)-2-(3,5-di-tert.-butyl-4-hydroxybenzylidene)- 1,4-thiazine-3-one (compound No. 10-5)

4-(6-cyanohexyl)-2-(3,5-di-tert.-butyl-4-hydroxybenzylidene)- 4-thiazine-3-one (compound No. 10-6)

Example 11

4-cyanomethyl-2-(3 , 5-di-tert.-butyl-4-hydroxybenzylidene)thiomorpholine- 3-one (compound No. 11-1)

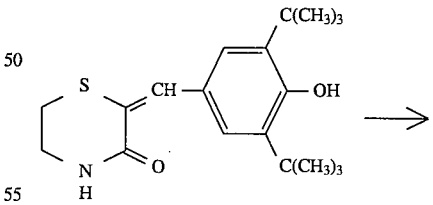

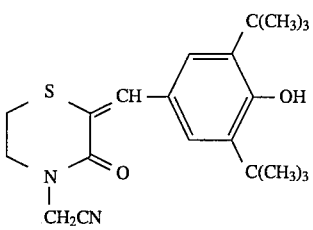

To a solution of 2-(3,5-di-tert.-butyl-4-hydroxybenzylidene)thiomorpholine- 3-one (reference compound No.

4-1, 1.00 g) in tetrahydrofuran (200 ml), n-butyl lithium (1.6M, 3.74 ml) was added dropwise under a nitrogen atmosphere and ice-salt cooling. The mixture was stirred for 30 minutes at room temperature. To the mixture, bromoacetonitrile (0.44 ml) dissolved in tetrahydrofuran (10 ml) was added and the mixture was stirred for 18 hours at room temperature. Water was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 0.35 g (31.4%) of the titled compound.

mp 172.8°–173.7° C.

IR (KBr, cm$^{-1}$) 3627, 2958, 1736, 1629, 1561, 1482, 1436, 1337, 1237, 1209, 1160, 1094, 904, 737

The following compounds can be prepared by a method similar to Example 11 using a reference compound 4-1- 4-3 for a starting material.

4-(3-cyanopropyl)-2-(3,5-di-tert.-butyl-4-hydroxybenzylidene)thiomorpholine- 3-one (compound No. 11-2)

4-cyanomethyl-2-[5-tert.-butyl-3-[1,1-dimethyl-2-(tetrahydropyran- 2-yloxy)ethyl]-4-hydroxybenzylidene]thiomorpholine-3-one (compound No. 11-3)

4-cyanomethyl-2-(3 , 5-di-tert.-butyl-4-methoxymethoxybenzylidene)thiomorpholine- 3-one (compound No. 11- 4)

Example 12

2-(4-acetoxy-3,5-diisopropylbenzylidene)-4-cyanomethyl-1,4-thiazine- 3-one (compound No. 12-1)

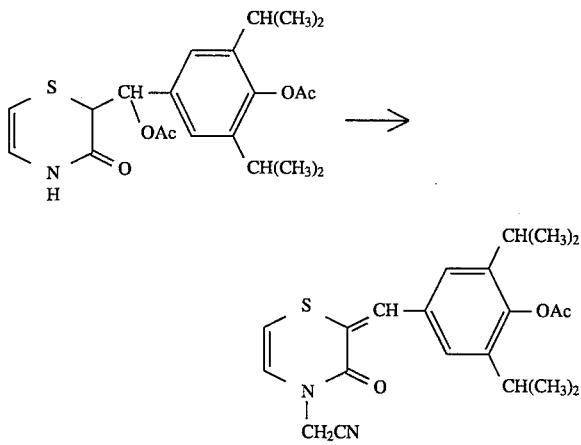

To a suspension of sodium hydride (60% suspension in paraffin liquid, 0.12 g) in tetrahydrofuran (2 ml), 2-(α,4-diacetoxy- 3,5-diisopropylbenzyl)-1,4-thiazine-3-one (reference compound No.5-1, 1.00 g) dissolved in tetrahydrofuran (12 ml) was added dropwise under a nitrogen atmosphere and ice cooling. The mixture was stirred for 15 minutes at room temperature. To the mixture, bromoacetonitrile (0.19 ml) was added and the mixture was stirred for 1 hour at room temperature. Dilute hydrochloric acid was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 0.70 g (74%) of the titled compound.

mp 181°–185° C.

IR (KBr, cm$^{-1}$) 3075, 2966, 2870, 2241, 1763, 1652, 1593, 1575, 1470, 1420, 1385, 1368, 1353, 1310, 1267, 1218

The following compounds can be prepared by a method similar to Example 12 using a reference compound 5-2- 5-6 for a starting material.

2-(4-benzoyloxy-3,5-diisopropylbenzylidene)-4-cyanomethyl-1,4-thiazine- 3-one (compound No. 12-2)

2-(4-acetoxy-3-tert.-butylbenzylidene)-4-cyanomethyl-1, 4-thiazine- 3-one (compound No. 12-3)

2-(4-acetoxy-3,5-dimethylbenzylidene)-4-cyanomethyl-1,4-thiazine- 3-one (compound No. 12-4)

2-(4-acetoxy-5-methoxy-3-methylbenzylidene)-4-cyanomethyl-1,4-thiazine- 3-one (compound No. 12-5)

2-(4-acetoxy-5-tert.-butyl-3-dimethylaminomethylbenzylidene)-4-cyanomethyl- 1,4-thiazine-3-one (compound No. 12-6)

Example 13

2-(4-acetoxy-3 , 5-diisopropylbenzylidene)-4-cyanomethylthiomorpholine- 3-one (compound No. 13-1)

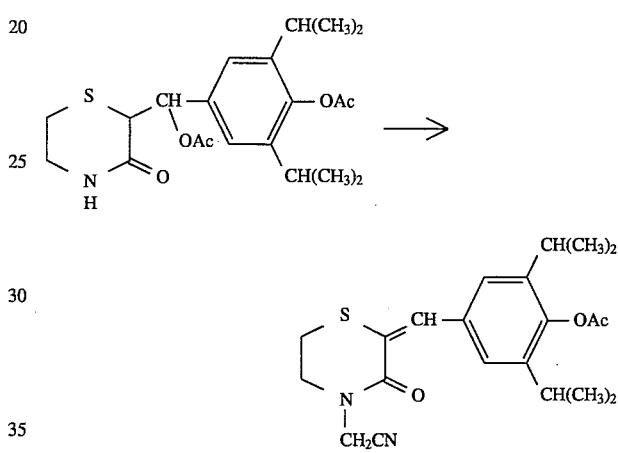

To a suspension of sodium hydride (60% suspension in paraffin liquid, 0.32 g) in tetrahydrofuran (15 ml), 2-(α,4-diacetoxy- 3,5-diisopropylbenzyl)thiomorphorine-3-one (reference compound No.6-1, 1.50 g) dissolved in tetrahydrofuran (15 ml) was added dropwise under a nitrogen atmosphere. The mixture was stirred for 1 hour at room temperature. To the mixture, bromoacetonitrile (0.52 ml) was added and the mixture was stirred for 2 hours at 60° C. The mixture was poured into dilute hydrochloric acid, and the whole was extracted with ethyl acetate. The organic layer was washed with saturated sodium chloride solution, dried over anhydrous magnesium sulfate and concentrated in vacuo. The oily residue was purified by silica gel column chromatography to give 0.67 g (47%) of the titled compound.

IR (Film, cm$^{-1}$) 2964, 2930, 2871, 2253, 1759, 1641, 1590, 1573, 1470, 1435, 1421, 1385, 1370

The following compounds can be prepared by a method similar to Example 13 using a reference compound 6-2- 6-6 for a starting material.

2-(4-benzoyloxy-3 , 5-diisopropylbenzylidene)-4-cyanomethylthiomorpholine- 3-one (compound No. 13-2)

2-(4-acetoxy-3-tert.-butylbenzylidene)-4-cyanomethylthiomorpholine- 3-one (compound No. 13-3)

mp 126.5°–128.0° C.

IR (KBr, cm$^{-1}$) 1703, 1674, 1490, 1375, 1330, 1254, 1234, 1188, 1167, 1134, 1094

2-(4-acetoxy-3,5-dimethylbenzylidene)-4-cyanomethylthiomorpholine- 3-one (compound No. 13-4)

mp 141.5°–144.5° C.

IR (KBr, cm⁻¹) 2990, 2950, 2916, 2246, 1748, 1629, 1601, 1570, 1484, 1442, 1423, 1411

2-(4-acetoxy-5-methoxy-3-methylbenzylidene)-4-cyanomethylthiomorpholine-one (compound No. 13-5)

2-(4-acetoxy-5-tert.-butyl-3-dimethylaminomethylbenzylidene)-4-cyanomethylthiomorpholine- 3-one (compound No. 13-6)

Example 14

2-(3,5-di-tert.-butyl-4-hydroxybenzylidene)-4-(1H-tetrazol-5-ylmethyl)- 1,4-thiazine-3-one (compound No. 14-1)

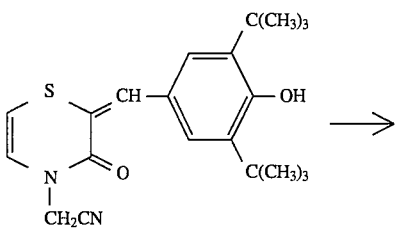

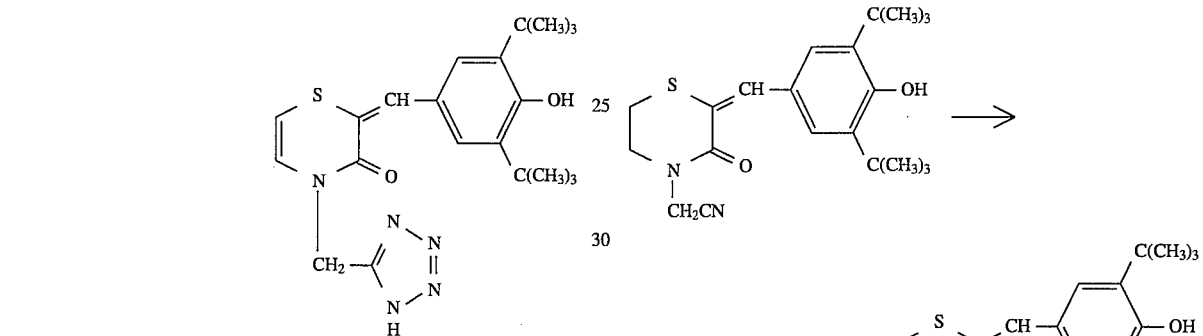

To a solution of 4-cyanomethyl-2-(3,5-di-tert.-butyl-4-hydroxybenzylidene)- 1,4-thiazine-3-one (compound No. 10-1, 0.40 g) in dimethylformamide (10 ml), sodium azide (0.14 g) and ammonium chloride (0.12 g) were added. The mixture was stirred for 2 hours at 110° C. Saturated sodium chloride solution was added to the mixture, and the whole was extracted with ethyl acetate. The organic layer was washed with saturated sodium chloride solution, dried over anhydrous magnesium sulfate and concentrated in vacuo. The oily residue was purified by silica gel column chromatography to give 0.22 g (49%) of the titled compound.

mp 183.8°–186.2° C.

IR (KBr, cm⁻¹) 3627, 3090, 2956, 1651, 1612, 1560, 1541, 1438, 1422, 1392, 1352, 1316, 1282

The following compounds can be prepared by a method similar to Example 14 using a compound 10-2, 10-5, 10-6, 12-1- 12-6 or 29-1 for a starting material.

2-(3,5-di-tert.-butyl-4-hydroxybenzylidene)-4-[3-(1H-tetrazol-5-yl)propyl)- 1,4-thiazine-3-one (compound No. 14-2)

2-(3,5-diisopropyl-4-hydroxybenzylidene)-4-(1H-tetrazol-5-ylmethyl)- 1,4-thiazine-3-one (compound No. 14-3)

mp 177.4°–178.6° C. (n-hexane - ethyl acetate)

IR (KBr, cm⁻¹) 3212, 2964, 1617, 1584, 1561, 1536, 1470, 1427, 1395, 1356, 1294, 1271, 1241, 1202, 1176

2-(3-tert.-butyl-4-hydroxybenzylidene)-4-(1H-tetrazol-5-ylmethyl)- 1,4-thiazine-3-one (compound No. 14-4)

2-(3,5-dimethyl-4-hydroxybenzylidene)-4-(1H-tetrazol-5-ylmethyl)- 1,4-thiazine-3-one (compound No. 14-5)

2-(4-hydroxy-5-methoxy-3-methylbenzylidene)-4-(1H-tetrazol-5-ylmethyl)- 1,4-thiazine-3-one (compound No. 14-6)

2-(5-tert.-butyl-3-dimethylaminomethyl-4-hydroxybenzylidene)-4-( 1H-tetrazol-5-ylmethyl)-1,4-thiazine-3-one (compound No. 14-7)

2-(3,5-di-tert.-butyl-4-hydroxybenzylidene)-4-[7-(1H-tetrazol-5-yl)heptyl)- 1,4-thiazine-3-one (compound No. 14-8)

2-(3,5-di-tert.-butyl-4-hydroxybenzylidene)-4-[2-(1H-tetrazol-5-yl)ethyl]-1,4-thiazine-3-one (compound No. 14-9)

mp 235° C. (about)

IR (KBr, cm⁻¹) 3611, 3124, 3085, 2950, 2897, 1649, 1604, 1579, 1554, 1440, 1418, 1365, 1310, 1288, 1257

2-(3,5-di-tert.-butyl-4-hydroxybenzylidene)-4-[6-(1H-tetrazol-5-yl)hexyl)- 1,4-thiazine-3-one (compound No. 14-10)

Example 15

2-(3,5-di-tert.-butyl-4-hydroxybenzylidene)-4-(1H-tetrazol-5-ylmethyl)thiomorphorine- 3-one (compound No. 15-1)

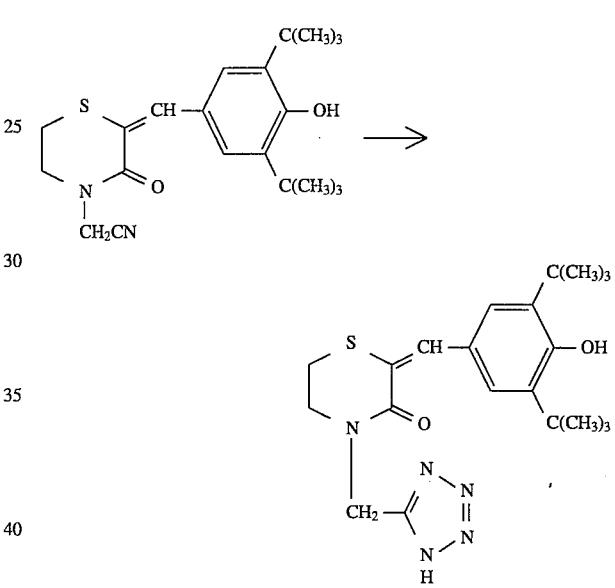

To a solution of 4-cyanomethyl-2-(3,5-di-tert.-butyl-4-hydroxybenzylidene)thiomorpholine- 3-one (compound No. 11-1, 0.29 g) in dimethylformamide (7 ml), sodium azide (73 mg) and ammonium chloride (60 mg) were added. The mixture was stirred for 8 hours at 110° C. Saturated sodium chloride solution was added to the mixture, and the whole was extracted with ethyl acetate. The organic layer was dried over anhydrous magnesium sulfate and concentrated in vacuo. The oily residue was purified by silica gel column chromatography to give 0.14 g (41.4%) of the titled compound.

mp 229.2°–230.1° C. (n-hexane - ethyl acetate)

IR (KBr, cm⁻¹) 3618, 2956, 1607, 1563, 1536, 1482, 1438, 1420, 1316, 1267, 1209, 1148, 1084

The following compounds can be prepared by a method similar to Example 15 using a compound 11-2 or 13-1- 13-6 of a starting material.

2-(3,5-di-tert.-butyl-4-hydroxybenzylidene)-4-[3-(1H-tetrazol-5-yl)propyl)thiomorpholine- 3-one (compound No. 15-2)

2-(3,5-diisopropyl-4-hydroxybenzylidene)-4-(1H-tetrazol-5-ylmethyl)thiomorpholine- 3-one (compound No. 15-3)

mp 197.3°–198.5° C. (n-hexane - ethyl acetate)

IR (KBr, cm$^{-1}$) 3281, 2963, 1613, 1567, 1534, 1470, 1427, 1374, 1360, 1344, 1306, 1274, 1237, 1208, 1175, 1156

2-(3-tert.-butyl-4-hydroxybenzylidene)-4-(1H-tetrazol-5-ylmethyl)-thiomorpholine- 3-one (compound No. 15-4)

mp over 250° C.

IR (KBr, cm$^{-1}$) 3315, 1631, 1585, 1557, 1341, 1228, 1096, 1057, 907, 833

2-(3,5-dimethyl-4-hydroxybenzylidene)-4-(1H-tetrazol-5-ylmethyl)thiomorpholine- 3-one (compound No. 15-5)

mp 225.0°–229.0° C. (ethyl acetate - ethanol)

IR (KBr, cm$^{-1}$) 3299, 2981, 2907, 2768, 2640, 1605, 1589, 1554

2-4-hydroxy-5-methoxy-3-methylbenzylidene)-4-(1H-tetrazol-5-ylmethyl)thiomorpholine- 3-one (compound No. 15-6)

2-(5-tert.-butyl-3-dimethylaminomethyl-4-hydroxybenzylidene)-4-( 1H-tetrazol-5-ylmethyl)thiomorpholine-3-one (compound No. 15-7)

Example 16

2-(3 , 5-di-tert.-butyl-4-hydroxybenzylidene)-4-methoxycarbonylmethylthiomorpholine- 3-one (compound No. 16-1)

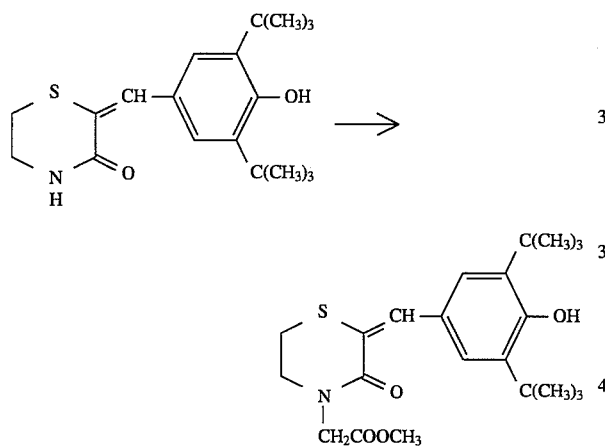

To a suspension of sodium hydride (60% suspension in paraffin liquid, 0.05 g) in tetrahydrofuran (2 ml), 2-(3,5-di-tert.-butyl- 4-hydroxybenzylidene)thiomorpholine-3-one(reference compound No.4-1, 0.20 g) dissolved in tetrahydrofuran (2 ml) was added dropwise under a nitrogen atmosphere and ice cooling. The mixture was stirred for 30 minutes at room temperature. To the mixture, methyl bromoacetate (0.06 ml) was added and the mixture was stirred for 2 days at 60° C. Dilute hydrochloric acid was added to the mixture and the whole was extracted with ethyl acetate. The organic layer was washed with saturated sodium chloride solution, dried over anhydrous magnesium sulfate and concentrated in vacuo. The oily residue was purified by silica gel column chromatography to give 0.24 g (99%) of the titled compound.

mp 159.3°–163.9° C.

IR (KBr, cm$^{-1}$) 3358, 2998, 2955, 2870, 1748, 1615, 1567, 1473, 1436, 1418, 1364, 1343, 1309

The following compounds can be prepared by a method similar to Example 16.

2-(3 , 5-di-tert.-butyl-4-hydroxybenzylidene)-4-ethoxycarbonylmethylthiomorpholine- 3-one (compound No. 16-2)

2-(3 , 5-di-tert.-butyl-4-hydroxybenzylidene)-4-(3-methoxycarbonylpropyl)thiomorpholine- 3-one (compound No. 16-3)

2-(3,5-di-tert.-butyl-4-hydroxybenzylidene)-4-(7-methoxycarbonylheptyl)thiomorpholine- 3-one (compound No. 16-4)

2-(3,5-di-tert.-butyl-4-hydroxybenzylidene)-4-(6-methoxycarbonylhexyl)thiomorpholine- 3-one (compound No. 16-5)

Example 17

2-(4-acetoxy-3 , 5-diisopropylbenzylidene)-4-methoxycarbonylmethyl- 1,4-thiazine-3-one (compound No.17-1)

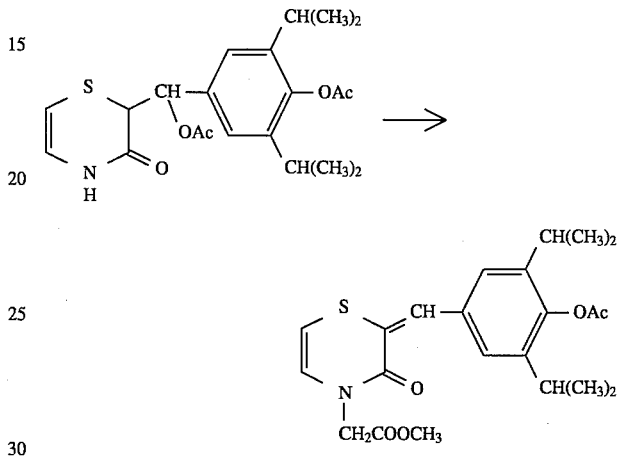

To a suspension of sodium hydride (60% suspension in paraffin liquid, 0.12 g) in tetrahydrofuran (3 ml), 2-(α,4-diacetoxy- 3,5-diisopropylbenzyl)-1,4-thiazine-3-one (reference compound No.5-1, 1.00 g) dissolved in tetrahydrofuran (10 ml) was added dropwise under a nitrogen atmosphere and ice cooling. The mixture was stirred for 10 minutes at room temperature. To the mixture, methyl bromoacetate (0.23 ml) was added and the mixture was stirred for 1 hour at room temperature. Dilute hydrochloric acid was added to the mixture and the whole was extracted with ethyl acetate. The organic layer was washed with saturated sodium chloride solution, dried over anhydrous magnesium sulfate and concentrated in vacuo. The oily residue was purified by silica gel column chromatography to give 0.95 g (92%) of the titled compound.

mp 126.4°–133.5° C.

IR (KBr, cm$^{-1}$) 3077, 3024, 2965, 2934, 2871, 1760, 1654, 1593, 1573, 1468, 1455, 1436, 1418, 1381, 1335, 1283, 1270, 1244

The following compounds can be prepared by a method similar to Example 17 using a reference compound 5-1- 5-6 for a starting material.

2-(4-acetoxy-3,5-diisopropylbenzylidene)-4-ethoxycarbonylmethyl- 1,4-thiazine-3-one (compound No. 17-2)

2-(4-benzoyloxy-3,5-diisopropylbenzylidene)-4-ethoxycarbonylmethyl- 1,4-thiazine-3-one (compound No. 17-3)

2-(4-acetoxy-3 , 5-diisopropylbenzylidene)-4-(3-methoxycarbonylpropyl)- 1,4-thiazine-3-one (compound No. 17-4)

2-(4-acetoxy-3-tert.-butylbenzylidene)-4-methoxycarbonylmethyl- 1,4-thiazine-3-one (compound No. 17-5)

2-(4-acetoxy-3,5-dimethylbenzylidene)-4-methoxycarbonylmethyl- 1,4-thiazine-3-one (compound No. 17-6)

2-(4-acetoxy-5-methoxy-3-methylbenzylidene)-4-methoxycarbonylmethyl- 1,4-thiazine-3-one (compound No. 17-7)

2-(4-acetoxy-5-tert.-butyl-3-dimethylaminomethylbenzylidene)-4-methoxycarbonylmethyl- 1,4-thiazine-3-one (compound No. 17-8)

Example 18

2-(4-acetoxy-3,5-diisopropylbenzylidene)-4-methoxycarbonylmethylthiomorpholine- 3-one (compound No. 18-1)

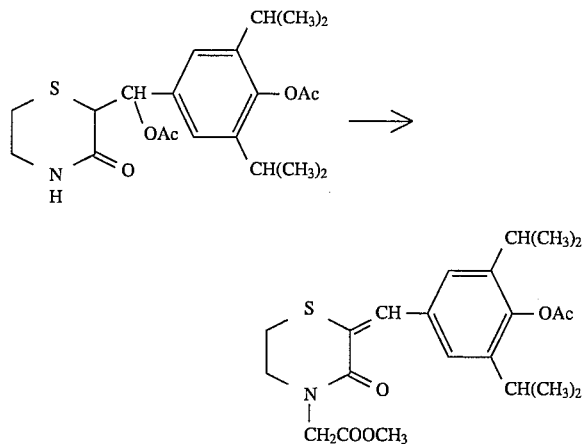

To a suspension of sodium hydride (60% suspension in paraffin liquid, 0.15 g) in tetrahydrofuran (5 ml), 2-(α,4-diacetoxy- 3,5-diisopropylbenzyl)thiomorpholine-3-one (reference compound No.6-1, 0.70 g) dissolved in tetrahydrofuran (12 ml) was added dropwise under a nitrogen atmosphere. The mixture was stirred for 40 minutes at room temperature. To the mixture, methyl bromoacetate (0.18 ml) was added and the mixture was stirred for 3 days at 60° C. After cooling, the mixture was poured into dilute hydrochloric acid and the whole was extracted with ethyl acetate. The organic layer was washed with saturated sodium chloride solution, dried over anhydrous magnesium sulfate and concentrated in vacuo to give 0.65 g (90%) of the titled compound.

mp 148.7°–149.9° C.

IR (KBr, cm$^{-1}$) 2957, 2936, 2870, 1765, 1741, 1641, 1589, 1570, 1469, 1438, 1421, 1405, 1373

The following compounds can be prepared by a method similar to Example 18 using a reference compound 6-1-6-6 for a starting material.

2-(4-acetoxy-3,5-diisopropylbenzylidene)-4-ethoxycarbonylmethyl-thiomorpholine- 3-one (compound No. 18-2)

2-(4-acetoxy-3,5-diisopropylbenzylidene)-4-(3-methoxycarbonylpropyl)thiomorpholine- 3-one (compound No. 18-3)

2-(4-benzoyloxy-3 , 5-diisopropylbenzylidene)-4-methoxycarbonylmethylthiomorpholine- 3-one (compound No. 18-4)

2(4-acetoxy-3-tert.-butylbenzylidene)-4-methoxycarbonylmethyl-thiomorpholine- 3-one (compound No. 18-5)

2(4-acetoxy-3,5-dimethylbenzylidene)-4-methoxycarbonylmethyl-thiomorpholine- 3-one (compound No. 18-6)

2-(4-acetoxy-5-methoxy-3-methylbenzylidene)-4-methoxycarbonylmethylthiomorpholine- 3-one (compound No. 18-7)

mp 110.0°–113.5° C.

IR (KBr, cm$^{-1}$) 2939, 1759, 1737, 1627, 1589, 1206, 1149, 1101, 1011, 909, 844, 742

2-(4-acetoxy-5-tert.-butyl-3-dimethylaminomethylbenzylidene)-4-methoxycarbonylmethylthiomorpholine- 3-one (compound No. 18-8);

Example 19

4-carboxymethyl-2-(3,5-di-tert.-butyl-4-hydroxybenzylidene)-1,4-thiazine- 3-one (compound No. 19-1)

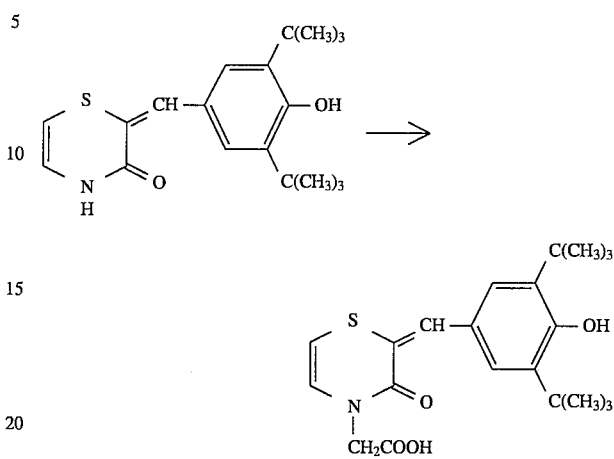

To a suspension of sodium hydride (60% suspension in paraffin liquid, 0.53 g) in tetrahydrofuran (10 ml), 2-(3,5-di-tert.-butyl- 4-hydroxybenzylidene)-1,4-thiazine-3-one (reference compound No.3-1, 2.00 g) dissolved in tetrahydrofuran (25 ml) was added dropwise under a nitrogen atmosphere. The mixture was stirred for 40 minutes at room temperature. To the mixture, ethyl bromoacetate (0.74 ml) was added and the mixture was stirred for 15 minutes at room temperature. Dilute hydrochloric acid was added to the mixture and the whole was extracted with ethyl acetate. The organic layer was washed with saturated sodium chloride solution, dried over anhydrous magnesium sulfate and concentrated in vacuo. The oily residue was dissolved in tetrahydrofuran (10 ml). To the solution, lithium hydroxide monohydrate (2.53 g) dissolved in water (10 ml) was added at 0° C. and the mixture was stirred for 30 minutes at 0° C. Dilute hydrochloric acid was added to the mixture and the whole was extracted with ethyl acetate. The organic layer was washed with saturated sodium chlorided solution, dried over anhydrous magnesium sulfate and concentrated in vacuo. The oily residue was purified by silica gel column chromatography to give 0.76 g (63%) of the titled compound.

mp 207.7°–209.2° C. (hexane - ethyl acetate)

IR (KBr, cm$^{-1}$) 3624, 3078, 2956, 1737, 1642, 1563, 1438, 1421, 1244, 1212, 1160

The following compounds can be prepared by a method similar to Example 19 using a reference compound 3-1 or 3-2 for a starting material.

4-(3-carboxypropyl)-2-(3,5-di-tert.-butyl-4-hydroxybenzylidene)- 1,4-thiazine-3-one (Compound No. 19-2)

2-[5-tert.-butyl-3-[1,1-dimethyl-2-(tetrahydropyran-2-yloxy)ethyl]-4-carboxymethyl-4-hydroxybenzylidene]-1,4-thiazine- 3-one (compound No. 19-3)

4-(7-carboxyheptyl)-2-(3,5-di-tert.-butyl-4-hydroxybenzylidene)- 1,4-thiazine-3-one (compound No. 19-4)

Example 20

4-carboxymethyl-2-(3,5-diisopropyl-4-hydroxybenzylidene)-1,4-thiazine- 3-one (compound No. 20-1)

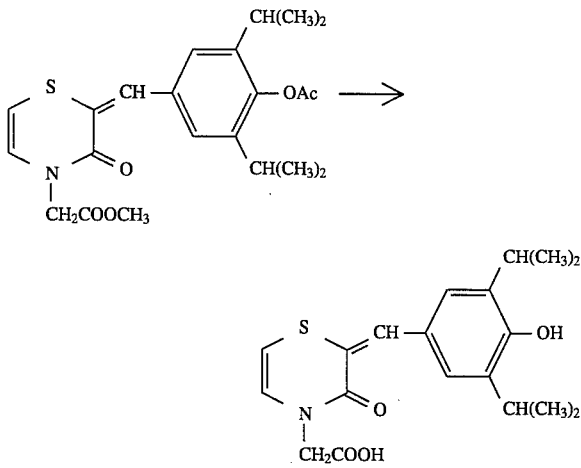

To a solution of 2-(4-acetoxy-3,5-diisopropylbenzylidene)- 4-methoxycarbonylmethyl-1,4-thiazine-3-one (compound No.17-1, 0.89 g) in a mixture of tetrahydrofuran (10 ml) and methanol (4 ml), lithium hydroxide monohydrate (0.89 g) dissolved in water (10 ml) was added and the mixture was stirred for 2 hours at room temperature. Dilute hydrochloric acid was added to the mixture to acidify it and the whole was extracted with ethyl acetate. The organic layer was washed with saturated sodium chloride solution, dried over anhydrous magnesium sulfate and concentrated in vacuo to give 0.62 g (81%) of the titled compound.

mp 121.8°–123.7° C. (hexane - ethyl acetate)

IR (KBr, cm$^{-1}$) 3410, 2964, 1728, 1634, 1596, 1561, 1469, 1429, 1407, 1379, 1362, 1339, 1270, 1195

The following compounds can be prepared by a method similar to Example 20 using a compound 17-4- 17-8 for a starting material.

4-(3-carboxypropyl)-2-(3,5-diisopropyl-4-hydroxybenzylidene)- 1,4-thiazine-3-one (compound No. 20-2)

2-(3-tert.-butyl-4-hydroxybenzylidene)-4-carboxymethyl-1,4-thiazine- 3-one (compound No. 20-3)

4-carboxymethyl-2-(3,5-dimethyl-4-hydroxybenzylidene)-1,4-thiazine- 3-one (compound No. 20-4)

4-carboxymethyl-2-(4-hydroxy-5-methoxy-3-methylbenzylidene)-1,4-thiazine- 3-one (compound No. 20-5)

2-(5-tert.-butyl-3-dimethylaminomethyl-4-hydroxybenzylidene)-4-carboxymethyl- 1,4-thiazine-3-one (compound No. 20-6)

Example 21

4-carboxymethyl-2-(3 , 5-di-tert.-butyl -4-hydroxybenzylidene)thiomorpholine- 3-one (compound No. 21-1)

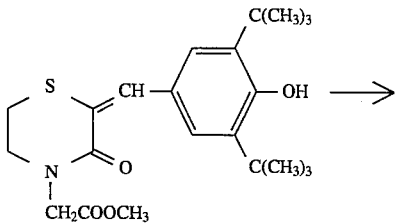

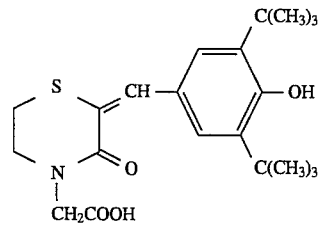

To a solution of 2-(3,5-di-tert.-butyl-4-hydroxybenzylidene)- 4-methoxycarbonylmethylthiomorpholine-3-one (compound No.16-1, 0.73 g) in tetrahydrofuran (3 ml), lithium hydroxide monohydrate (0.76 g) dissolved in water (2 ml) was added under ice cooling and the mixture was stirred for 1 hour. Dilute hydrochloric acid was added to the mixture to acidify it and the whole was extracted with ethyl acetate. The organic layer was washed with saturated sodium chloride solution, dried over anhydrous magnesium sulfate and concentrated in vacuo to give 0.56 g (79%) of the titled compound.

mp 212.2°–218.5° C. (hexane - ethyl acetate)

IR (KBr, cm$^{-1}$) 3618, 3580, 2957, 1736, 1607, 1558, 1479, 1440, 1421, 1397, 1374, 1359, 1338

The following compounds can be prepared by a method similar to Example 21 using a compound 16-3, 16-4 or 18-1- 18-8 for a starting material.

4-(3-carboxypropyl)-2-(3,5-di-tert.-butyl-4-hydroxybenzylidene)thiomorpholine- 3-one (compound No. 21-2)

4-(7-carboxyheptyl)-2-(3,5-di-tert.-butyl-4-hydroxybenzylidene)thiomorpholine- 3-one (compound No. 21-3)

4-carboxymethyl-2-(3,5-diisopropyl-4-hydroxybenzylidene)thiomorpholine- 3-one (compound No. 21-4)

mp 151.7°–152.8° C. (n-hexane - ethyl acetate)

IR (KBr, cm$^{-1}$) 3322, 2960, 1720, 1623, 1598, 1562, 1469, 1437, 1391, 1345, 1308, 1273, 1253, 1198

4-(3-carboxypropyl)-2-(3,5-diisopropyl-4-hydroxybenzylidene)thiomorpholine- 3-one (compound No. 21-5)

2-(3-tert.-butyl-4-hydroxybenzylidene)-4-carboxymethylthiomorpholine- 3-one (compound No. 21-6)

4-carboxymethyl-2-(3,5-dimethyl-4-hydroxybenzylidene)thiomorpholine- 3-one (compound No. 21-7)

4-carboxymethyl-2-(4-hydroxy-5-methoxy-3-methylbenzylidene)thiomorpholine- 3-one (compound No. 21-8)

mp 205.5°–208.5° C. (ethyl acetate, dec.)

IR (KBr, cm$^{-1}$) 3552, 2964, 1719, 1607, 1479, 1309, 1220, 1159, 1089, 835, 620

2-(5-tert.-butyl-3-dimethylaminomethyl-4-hydroxybenzylidene)-4-carboxymethylthiomorpholine- 3-one (compound No. 21-9)

Example 22

2-(3,5-di-tert.-butyl-4-hydroxybenzylidene)-4-methoxycarbonylmethyl- 3-thioxothiomorpholine (compound No. 22-1)

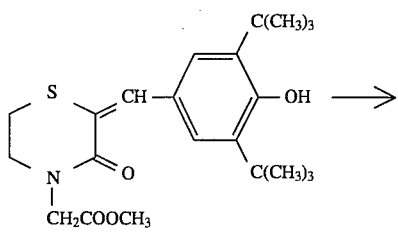

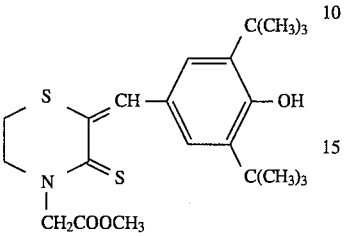

To a solution of 2-(3,5-di-tert.-butyl-4-hydroxybenzylidene)- 4-methoxycarbonylmethylthiomorpholine-3-one (compound No. 16-1, 0.69 g ) in toluene (40 ml), Lawesson's agent (1.38 g) was added. The mixture was refluxed for 15 hours and concentrated in vacuo. The oily residue was purified by silica gel column chromatography to give 0.25 g (35%) of the titled compound.

mp 136.4°–138.4° C. (hexane - ethyl acetate)

IR (KBr, cm$^{-1}$) 3587, 2959, 1742, 1583, 1494, 1439, 1420, 1392, 1376, 1362, 1343, 1317, 1283

The following compounds can be prepared by a method similar to Example 22 using a compound 18-1 or 18-4- 18-8 for a starting material.

2-(4-acetoxy-3 , 5-diisopropylbenzylidene)-4-methoxycarbonylmethyl- 3-thioxothiomorpholine (compound No. 22-2)

2-(4-benzoyloxy-3 , 5-diisopropylbenzylidene)-4-methoxycarbonylmethyl- 3-thioxothiomorpholine (compound No. 22-3)

2-(4-acetoxy-3-tert.-butylbenzylidene)-4-methoxycarbonylmethyl- 3-thioxothiomorpholine (compound No. 22-4)

2-(4-acetoxy-3,5-dimethylbenzylidene)-4-methoxycarbonylmethyl-3-thioxothiomorpholine (compound No. 22-5)

2-(4-acetoxy-5-methoxy-3-methylbenzylidene)-4-methoxycarbonylmethyl- 3-thioxothiomorpholine (compound No. 22-6)

2-(4-acetoxy-5-tert.-butyl-3-dimethylaminomethylbenzylidene)-4-methoxycarbonylmethyl- 3-thioxothiomorpholine (compound No. 22-7)

Example 23

4-carboxymethyl-2-(3,5-di-tert.-butyl-4-hydroxybenzylidene)-3-thioxothiomorpholine (compound No. 23-1)

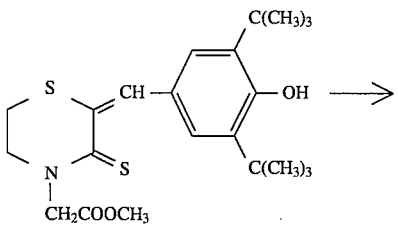

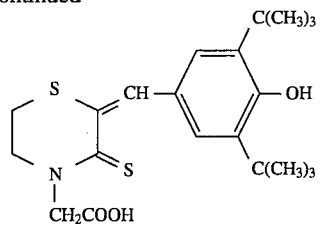

To a solution of 2-(3,5-di-tert.-butyl-4-hydroxy-benzylidene)- 4-methoxycarbonylmethyl-3-thioxothiomorpholine (compound No.22-1, 0.16 g) in tetrahydrofuran (5 ml), lithium hydroxide monohydrate (0.16 g) dissolved in a mixture of water (4 ml) and methanol (3 ml) was added under ice cooling and the mixture was stirred for 15 minutes at room temperature. 6N hydrochloric acid was added to the mixture and the whole was extracted with ethyl acetate. The organic layer was washed with saturated sodium chloride solution, dried over anhydrous magnesium sulfate and concentrated in vacuo to give 0.12 g (77%) of the titled compound.

mp 200°–208° C. (hexane - ethyl acetate)

IR (KBr, cm$^{-1}$) 3627, 2951, 1739, 1585, 1567, 1506, 1436, 1419, 1391, 1358, 1348, 1316, 1282, 1266, 1238

The following compounds can be prepared by a method similar to Example 23 using a compound or 22-1- 22-7 for a starting material.

4-carboxymethyl-2-(3,5-diisopropyl-4-hydroxybenzylidene)-3-thioxothiomorpholine (compound No. 23-2)

2-(3-tert.-butyl-4-hydroxybenzylidene)-4-carboxymethyl -3-thioxothiomorpholine (compound No. 23-3)

4-carboxymethyl-2-(3,5-dimethyl-4-hydroxybenzylidene)-3-thioxothiomorpholine (compound No. 23-4)

4-carboxymethyl-2-(4-hydroxy-5-methoxy-3-methylbenzylidene)-3-thioxothiomorpholine (compound No. 23-5)

2-(5-tert.-butyl-3-dimethylaminomethyl-4-hydroxybenzylidene)-4-carboxymethyl- 3-thioxothiomorpholine (compound No. 23-6)

Example 24

2-(3,5-di-tert.-butyl-4-hydroxybenzylidene)-4-sulfomethyl-1,4-thiazine- 3-one (compound No. 24-1)

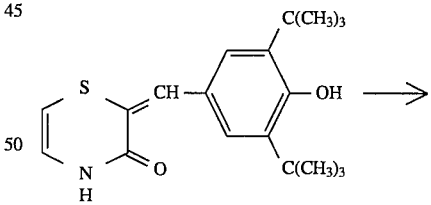

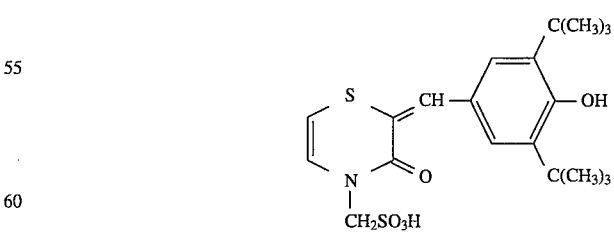

To a suspension of sodium hydride (60% suspension in paraffin liquid, 0.10 g) in tetrahydrofuran (2 ml), 2-(3,5-di-tert.-butyl- 4-hydroxybenzylidene)-1,4-thiazine-3-one (reference compound No.3-1, 0.20 g) dissolved in dimethylformaldehyde (2 ml) was added dropwise under a nitrogen atmosphere. The mixture was stirred for 10 minutes at room temperature. To the mixture, chloromethane sulfonic acid (0.20 g) dissolved in dimethylformaldehyde (1 ml) was added and the mixture was stirred for one night at 50° C. Saturated aqueous ammonium chloride solution was added to the mixture and the whole was extracted with ethyl acetate. The organic layer was washed with saturated sodium chlorided solution, dried over anhydrous magnesium sulfate and concentrated in vacuo. The oily residue was purified by silica gel column chromatography to give the titled compound.

The following compound can be prepared by a method similar to Example 24 using a reference compound 4-1 for a starting material.

2-(3 , 5-di-tert.-butyl-4-hydroxybenzylidene)-4-sulfomethylthiomorpholine- 3-one (compound No. 24-2)

Example 25

2-(3 , 5-di-tert.-butyl-4-hydroxybenzylidene)-4-methoxycarbonylmethylthiomorpholine (compound No. 25-1)

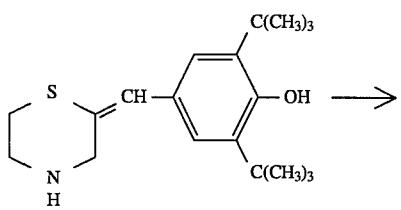

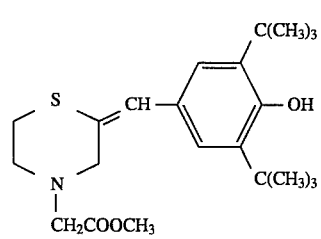

To a solution of 2-(3,5-di-tert.-butyl-4-hydroxybenzylidene)thiomorpholine (reference compound 7-1, 0.60 g) in dimethylformaldehyde (8 ml), potassium carbonate (0.26 g) and methyl bromoacetate (0.20 ml) were added. The mixture was stirred for 1 hour at room temperature. Water was added to the mixture and the whole was extracted with diethyl ether. The organic layer was washed with saturated sodium chloride solution, dried over anhydrous magnesium sulfate and concentrated in vacuo. The oily residue was purified by silica gel column chromatography to give 0.76 g (100%) of the titled compound.

IR (Film, cm$^{-1}$) 3635, 2954, 2872, 1747, 1517, 1435, 1392, 1361, 1309, 1202, 1155, 1120, 1023

Example 26

4-carboxymethyl-2-(3 , 5-di-tert.-butyl-4-hydroxybenzylidene)thiomorpholine (compound No. 26-1)

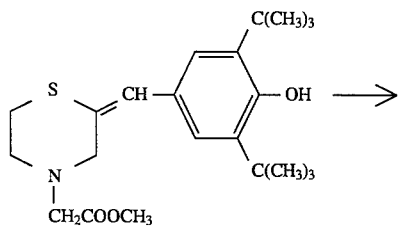

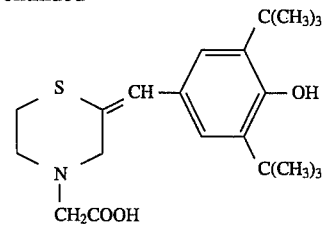

To a solution of 2-(3,5-di-tert.-butyl-4-hydroxy-benzylidene)- 4-methoxycarbonylmethylthiomorpholine (compound No.25-1, 0.74 g) in tetrahydrofuran (10 ml), lithium hydroxide monohydrate (1.98 g) dissolved in water (13 ml) and methanol (3 ml) were added under ice cooling. The mixture was stirred for 15 minutes at room temperature. 6N hydrochloric acid was added to the mixture and the whole was extracted with ethyl acetate. The organic layer was washed with saturated sodium chloride solution, dried over anhydrous magnesium sulfate and concentrated in vacuo to give 0.25 g (35%) of the titled compound.

IR (KBr, cm$^{-1}$) 3632, 3418, 2955, 1633, 1437, 1340, 1318, 1239, 1214, 1160, 1119, 1025, 890, 811, 792

Example 27

4-carbamoylmethyl-2-(3,5-diisopropyl-4-hydroxybenzylidene)-1,4-thiazine- 3-one (compound No. 27-1)

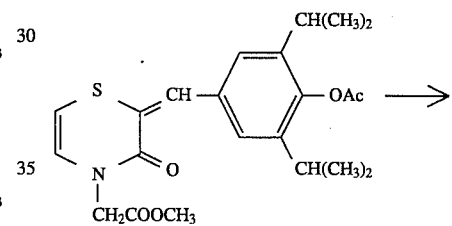

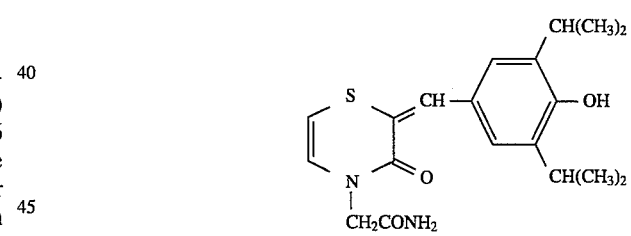

2-(4-Acetoxy-3,5-diisopropylbenzylidene)-4-methoxycarbonylmethyl- 1,4-thiazine-3-one(compound No.17-1, 0.1 g) was dissolved in ammonia/methanol(17.85N, 10 ml). To the solution, hydrochloric acid in methanol (0.1N, 2 ml) was added and the mixture was stirred in a sealed tube for 3 days at 80° C. The mixture was concentrated in vacuo and the whole was extracted with ethyl acetate. The organic layer was dried over anhydrous sodium sulfate and concentrated in vacuo. The oily residue was purified by silica gel column chromatography to give the titled compound.

IR (Film, cm$^{-1}$) 3337, 3080, 2961, 2926, 2869, 1682, 1634, 1557,1302, 1075, 992, 958

The following compound can be prepared by a method similar to Example 27.

2-(3 , 5-diisopropyl-4-hydroxybenzylidene)-4-(N-methylcarbamoylmethyl)- 1,4-thiazine-3-one (compound No. 27-2)

IR (Film, cm$^{-1}$) 3336, 2962, 2870, 1682, 1622, 1563, 1470, 1441

Example 28

2-(3,5-di-tert.-butyl-4-hydroxybenzylidene)-4-(2-phosphonoethyl)-1,4-thiazine-3-one (compound No. 28-1)

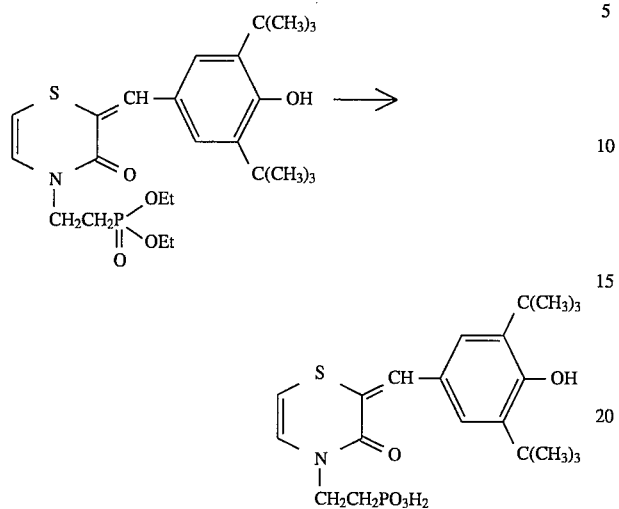

To a solution of 2-(3,5-di-tert.-butyl-4-hydroxybenzylidene)- 4-(2-phosphonoethyl)-1,4-thiazine-3-one diethyl ester (compound No. 8-1, 0.50 g) in dioxane (20 ml), 5.8N hydrochloric aid (14 ml) was added and the mixture was stirred for 1 hour at room temperature. The mixture was poured into dilute hydrochloric acid and the whole was extracted with diethyl ether. The organic layer was washed with saturated sodium chloride solution, dried over anhydrous magnesium sulfate and concentrated in vacuo. The oily residue was purified by silica gel column chromatography to give the titled compound.

The following compounds can be prepared by a method similar to Example 28 using a compound 8-2- 8-9 for a starting material.

2-[5-tert.-butyl-3-(1,1-dimethyl-2-hydroxyethyl)-4-hydroxybenzylidene]-4-(2-phosphonoethyl)-1,4-thiazine-3-one (compound No. 28- 2)

2-(4-acetoxy-3,5-diisopropylbenzylidene)-4-(2-phosphonoethyl)- 1,4-thiazine-3-one (compound No. 28-3)

2-(4-benzoyloxy-3,5-diisopropylbenzylidene)-4-(2-phosphonoethyl)- 1,4-thiazine-3-one (compound No. 28-4)

2-(4-acetoxy-3-tert.-butylbenzylidene)-4-(2-phosphonoethyl)-1,4-thiazine- 3-one (compound No. 28-5)

2-(4-acetoxy-3,5-dimethylbenzylidene)-4-(2-phosphonoethyl)-1,4-thiazine- 3-one (compound No. 28-6)

2-(4-acetoxy-5-methoxy-3-methylbenzylidene)-4-(2-phosphonoethyl)- 1,4-thiazine-3-one (compound No. 28-7)

2-(4-acetoxy-5-tert.-butyl-3-dimethylaminomethylbenzylidene)-4-( 2-phosphonoethyl)-1,4-thiazine-3-one (compound No. 28-8)

2-(3,5-di-tert.-butyl-4-hydroxybenzylidene)-4-(7-phosphonoheptyl)- 1,4-thiazine-3-one (compound No.28-9)

Example 29

4-(2-cyanoethyl)-2-(3,5-di-tert.-butyl-4-hydroxybenzylidene)- 1,4-thiazine-5-one (compound No. 29-1)

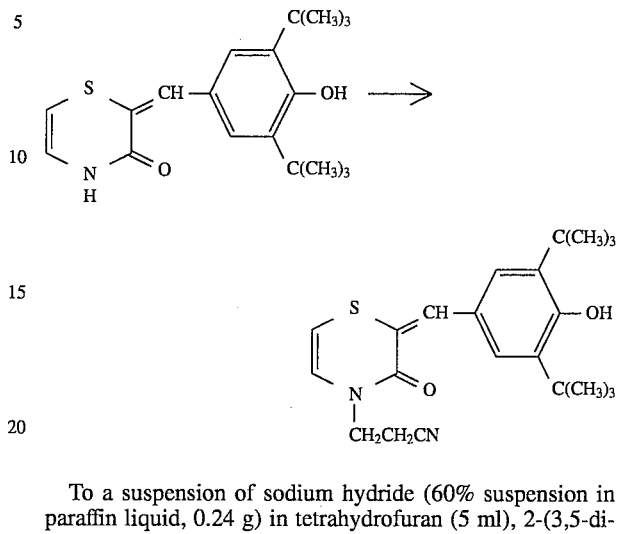

To a suspension of sodium hydride (60% suspension in paraffin liquid, 0.24 g) in tetrahydrofuran (5 ml), 2-(3,5-di-tert.-butyl- 4-hydroxybenzylidene)-1,4-thiazine-3-one (reference compound No. 3-1, 1.00 g) dissolved in tetrahydrofuran (8 ml) was added dropwise under a nitrogen atmosphere. The mixture was stirred for 20 minutes at room temperature. To the mixture, acrylnitrile (0.50 ml) was added and the mixture was stirred for 3 hours at room temperature. The mixture was poured into 1N hydrochloric acid, and the whole was extracted with ethyl acetate. The organic layer was washed with saturated sodium chloride solution, dried over anhydrous magnesium sulfate and concentrated in vacuo. The oily residue was purified by silica gel column chromatography to give 0.76 g (66%) of the titled compound.

mp 160.5°–164.8° C.

IR (KBr, cm$^{-1}$) 3628, 3564, 3084, 2959, 2252, 1638, 1586, 1564, 1438, 1420, 1393, 1359, 1328, 1308, 1289

Example 30

2-(3 , 5-di-tert.-butyl-4-hydroxybenzylidene)-4-(2-ethoxycarbonylethyl)- 1,4-thiazine-3-one (compound No. 29-1)

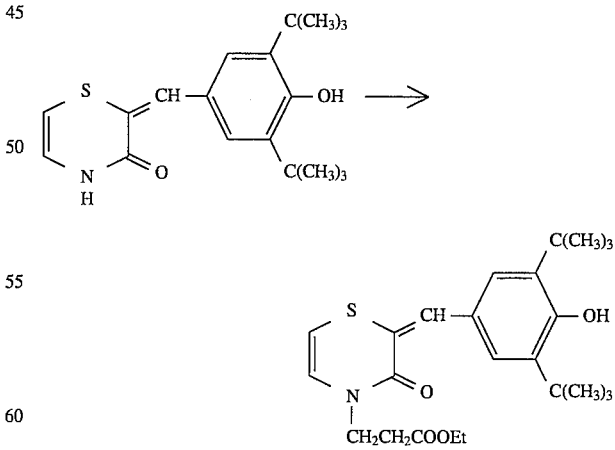

To a solution of 2-(3,5-di-tert.-butyl-4-hydroxybenzylidene)- 1,4-thiazine-3-one (reference compound No. 3-1, 0.60 g) in dimethylformamide (13 ml), potassium carbonate (0.50 g) and ethyl acrylate (0.49 ml) were added dropwise under a nitrogen atmosphere. The mixture was stirred for 1 hour at 110° C. After cooling, the mixture was poured into dilute hydrochloric acid, and the whole was extracted with ethyl ether. The organic layer was washed with saturated sodium chloride solution, dried over anhydrous magnesium sulfate and concentrated in vacuo. The oily residue was purified by silica gel column chromatography to give 0.56 g (72%) of the titled compound.

mp 101.7°–102.6° C.

IR (KBr, cm$^{-1}$) 3614, 2959, 1727, 1630, 1586, 1567, 1435, 1392, 1364, 1321, 1294, 1255, 1183, 1145

Example 31

4-(2-carboxyethyl)-2-(3,5-di-tert.-butyl-4-hydroxybenzylidene)- 1,4-thiazine-3-one (compound No. 31-1)

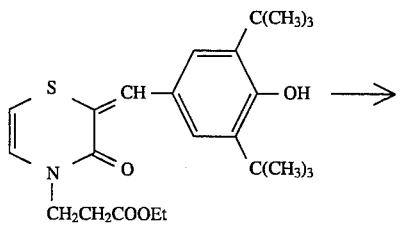

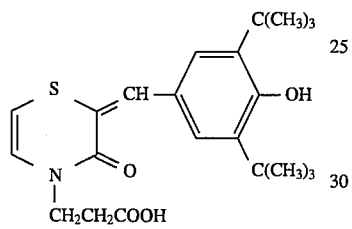

To a solution of 2-(3,5-di-tert.-butyl-4-hydroxybenzylidene)- 4-(2-ethoxycarbonylethyl)-1,4-thiazine-3-one (compound No.30-1, 0.51 g) in tetrahydrofuran (8 ml), lithium hydroxide monohydrate (0.50 g) dissolved in water (8 ml) and methanol (1 ml) were added under ice cooling and the mixture was stirred for 50 minutes. Dilute hydrochloric acid was added to the mixture and the whole was extracted with ethyl acetate. The organic layer was washed with saturated sodium chloride solution, dried over anhydrous magnesium sulfate and concentrated in vacuo. The oily residue was purified by silica gel column chromatography to give 0.37 g (77%) of the titled compound.

mp 200.6°–201.5° C. (n-hexane - ethyl acetate)

IR (KBr, cm$^{-1}$) 3620, 3207, 2956, 1732, 1650, 1617, 1584, 1559, 1434, 1401, 1362, 1333, 1282, 1263, 1149, 1120

FORMULATION

Examples of the formulations of the compounds of this invention are shown below.

| Tablet | | |
|---|---|---|
| compound of this invention | | 1 mg |
| lactose | | 131 mg |
| crystalline cellulose | | 35 mg |
| hydroxypropylcellulose | | 2 mg |
| magnesium stearate | | 1 mg |
| | total | 170 mg |
| compound of this invention | | 50 mg |
| lactose | | 140 mg |
| crystalline cellulose | | 45 mg |
| polyvinylpyrrolidone | | 3 mg |
| magnesium stearate | | 2 mg |
| | total | 240 mg |

| Granule | | |
|---|---|---|
| compound of this invention | | 100 mg |
| lactose | | 390 mg |
| polyvinylpyrrolidone | | 8 mg |
| magnesium stearate | | 2 mg |
| | total | 500 mg |

| Eye Drops | | |
|---|---|---|
| compound of this invention | | 0.5 g |
| conc. glycerol | | 1.5 g |
| hydrogenated castor oil | | 1.0 g |
| benzalkonium chloride | | 0.005 g |
| sodium edetate | | 0.01 g |
| dilute hydrochloric acid | | q.s. |
| sodium hydroxide | | q.s. |
| sterile purified water | | q.s. |
| | total | 100 ml |
| compound of this invention | | 3.0 g |
| conc. glycerol | | 1.0 g |
| polysorbate 80 | | 7.0 g |
| benzalkonium chloride | | 0.005 g |
| sodium edetate | | 0.01 g |
| dilute hydrochloric acid | | q.s. |
| sodium hydroxide | | q.s. |
| sterile purified water | | q.s. |
| | total | 100 ml |
| compound of this invention | | 0.01 g |
| conc. glycerol | | 2.0 g |
| polysorbate 80 | | 0.5 g |
| benzalkonium chloride | | 0.005 g |
| sodium edetate | | 0.01 g |
| dilute hydrochloric acid | | q.s. |
| sodium hydroxide | | q.s. |
| sterile purified water | | q.s. |
| | total | 100 ml |

| Eye Ointment | | |
|---|---|---|
| compound of this invention | | 1.0 g |
| liquid paraffine | | 10.0 g |
| white petrolatum | | 89.0 g |
| | total | 100.0 g |

PHARMACOLOGICAL TEST

In order to study the utility of the compounds of this invention, the protein stabilizing effect and the suppressive effect on lipid peroxide formation were examined.

1. Protein Stabilizing Effect

As a method of examining the protein stabilizing effect, a method for measuring an effect of a compound on the stability of bovine serum albumin against heat coagulation is known (Lancet, 1, 169 (1965)).

The protein stabilizing effect of the compound of this invention was examined according to the method described in the above-mentioned journal.

EXPERIMENTAL METHOD

Under ice cooling, bovine serum albumin (Sigma Chemical Company) was dissolved in 0.2M potassium phosphate buffer solution (pH 5.3) to adjust the concentration to 0.75%. To 2.7 ml of this albumin solution, 0.3 ml of a solution of a test compound in dimethyl sulfoxide was added and stirred. The reaction mixture was allowed to stand for 15 minutes at room temperature. After the solution was shaken for 2 minutes in a water bath at 67° C., the reaction was stopped by ice cooling. The temperature of the reaction mixture was raised to room temperature, and the absorbance, which is related to the white turbidity of water-soluble protein caused by heat coagulation, was measured at 660 nm of wave length.

The protein stabilizing effect of the compound of this invention was calculated by the following Formula.

$$\text{Protein stabilizing effect (\%)} = \frac{A_0 - A_1}{A_0} \times 100$$

$A_0$: absorbance in the case of absence of a test compound
$A_1$: absorbance in the case of presence of a test compound

RESULT

The experimental results are shown in Table 1.

TABLE 1

| Test compound | Concentration of test compound | Protein stabilizing effect |
|---|---|---|
| Compound No. 9-1 | $10^{-4}$M | 94.6% |
| Compound No. 14-1 | $10^{-4}$M | 99.5% |
| Compound No. 15-1 | $10^{-4}$M | 98.0% |
| Compound No. 19-1 | $10^{-4}$M | 98.2% |
| Compound No. 21-1 | $10^{-4}$M | 63.3% |

The compounds of this invention clearly inhibited the heat coagulation of protein significantly and showed excellent protein stabilizing effect.

2. Suppressive Effect on Lipid Peroxide Formation

Experimental Method

In 0.04M Tris buffer (containing 0.09M of potassium chloride, pH 7.4) containing a test compound, microsomes of rat liver, which was prepared according to Biochimica et Biophysica Acta, 618 (1980) 35–41, were reacted with ADP (13.2 mM), $Fe^{2+}$ (0.9 mM) and ascorbic acid (0.5 mM) for 15 minutes at 37° C. The amount of the produced lipid peroxide was measured by TBA method (Yagi et al., Biochem. Med., 15, 212 (1976)).

RESULT

The experimental results are shown in Table 2.

TABLE 2

| Test compound | Concentration of test compound | Suppressive effect on lipid peroxide formation |
|---|---|---|
| Compound No. 9-1 | $10^{-5}$M | 99.3% |
| Compound No. 14-1 | $10^{-5}$M | 100.0% |
| Compound No. 15-1 | $10^{-5}$M | 100.0% |
| Compound No. 19-1 | $10^{-5}$M | 99.5% |
| Compound No. 21-1 | $10^{-5}$M | 99.9% |

As shown in Table 2, each compound of this invention showed an excellent suppressive effect on lipid peroxide formation.

As shown in the results of the above Pharmacological Tests, the compound of this invention has both a protein stabilizing effect and a suppressive effect on lipid peroxide formation and it is expected that the compounds of this invention will be an excellent therapeutic agent for cataracts.

What we claim is:

1. A compound having the following formula (I) or a salt thereof,

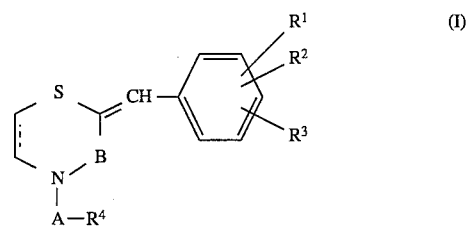

wherein $R^1$ is hydroxy or protected hydroxy;

$R^2$ is lower alkyl;

$R^3$ is hydrogen, lower alkyl, hydroxy, protected hydroxy, or lower alkoxy, and substituted lower alkyl wherein the substituent is hydroxy, or protected hydroxy, amino or lower alkylamino;

$R^4$ is carboxy or carboxy which is converted into ester or amide; tetrazolyl; phosphono or phosphono which is converted into ester or amide; sulfonyl or sulfonyl which is converted into ester or amide;

A is alkylene;

B is C=O, C=S or $CH_2$; and

----- is a single bond or a double bond.

2. A compound having the following formula (I) or a salt thereof,

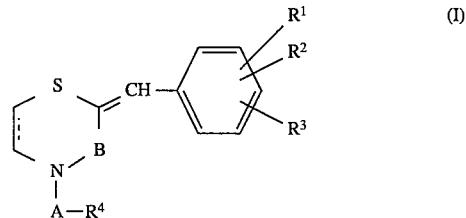

wherein $R^1$ is hydroxy, lower alkanoyloxy, lower alkylsulfonyloxy, arylsulfonyloxy, lower alkoxymethyloxy, benzoyloxy, benzyloxymethyloxy, tetrahydropyranyloxy or trimethylsilyloxy;

$R^2$ is lower alkyl;

$R^3$ is hydrogen, lower alkyl, hydroxy, lower alkanoyloxy, lower alkylsulfonyloxy, arylsulfonyloxy, lower alkoxymethyloxy, benzoyloxy, benzyloxymethyloxy, tetrahydropyranyloxy, trimethylsilyloxy, lower alkoxy, or substituted lower alkyl wherein the substituent is hydroxy, lower alkanoyloxy, lower alkylsulfonyloxy, arylsulfonyloxy, lower alkoxymethyloxy, benzoyloxy, benzyloxymethyloxy, tetrahydropyranyloxy, trimethylsilyloxy, amino or lower alkylamino;

$R^4$ is carboxy, carboxy which is converted into lower alkyl ester or aryl lower alkyl ester, carboxy which is converted into amide with ammonia, lower alkyl amine or aryl lower alkyl amine; tetrazolyl; phosphono, phosphono which is converted into lower alkyl or aryl lower alkyl ester; phosphono which is converted into amide with ammonia, lower alkylamine or aryl lower alkylamine; sulfonyl which is converted into lower alkyl or aryl lower alkyl ester; sulfonyl which is converted into amide with ammonia, lower alkylamine or aryl lower alkylamine;

A is alkylene;

B is C=O, C=S or $CH_2$ and

----- is a single bond or a double bond.

3. The compound or salt thereof of claim 2, wherein $R^1$ is hydroxy, lower alkanoyloxy or benzoyloxy;

$R^2$ is lower alkyl;

$R^3$ is hydrogen, lower alkyl, lower alkoxy, or substituted lower alkyl wherein the substituent is hydroxy, tetrahydropyranyloxy, amino or lower alkylamino;

$R^4$ is carboxy, carboxy which is converted into lower alkyl ester; carboxy which is converted into amide with ammonia or lower alkylamine; tetrazolyl; phosphono; phosphono which is converted into lower alkyl ester; sulfonyl which is converted into lower alkyl ester.

4. The compound or a salt thereof, as claimed in claim 2, wherein $R^1$ is hydroxy or lower alkanoyloxy;

$R^2$ is lower alkyl;

$R^3$ is hydrogen, lower alkyl or lower alkoxy;

$R^4$ is carboxy, carboxy which is converted into lower alkyl ester; carboxy which is converted into amide with ammonia or lower alkylamine; tetrazolyl; phosphono or phosphono which is converted into lower alkyl ester.

5. The compound or a salt thereof as claimed in claim 4, wherein $R^1$ is hydroxy or acetyloxy;

$R^2$ is methyl, isopropyl or tert.-butyl;

$R^3$ is hydrogen, methyl, isopropyl, tert.-butyl or methoxy;

$R^4$ is carboxy; carboxy which is converted into methyl or ethyl ester; carboxy which is converted into amide with ammonia or lower alkyl amine; tetrazolyl; phosphono or phosphono which is converted into ethyl ester;

A is methylene or ethylene;

B is C=O, C=S or $CH_2$, and

----- is a single bond.

6. The compound or a salt thereof as claimed in claim 4, wherein $R^1$ is hydroxy or acetyloxy;

$R^2$ is methyl, isopropyl or tert.-butyl;

$R^3$ is hydrogen, methyl, isopropyl, tert.-butyl or methoxy;

$R^4$ is carboxy; carboxy which is converted into methyl or ethyl ester; carboxy which is converted into amide with ammonia or lower alkyl amine; tetrazolyl; phosphono or phosphono which is converted into ethyl ester;

A is methylene;

B is C=O, and

----- is a single bond.

7. The compound or a salt thereof as claimed in claim 4, wherein $R^1$ is hydroxy or acetyloxy;

$R^2$ is isopropyl or tert.-butyl;

$R^3$ is isopropyl or tert.-butyl;

$R^4$ is carboxy; carboxy which is converted into methyl or ethyl ester; carboxy which is converted into amide with ammonia or lower alkyl amine; tetrazolyl; phosphono or phosphono which is converted into ethyl ester;

A is methylene or ethylene;

B is C=O, and

----- is a double bond.

8. The compound or a salt thereof as claimed in claim 4, wherein $R^1$ is hydroxy;

$R^2$ is tert.-butyl;

$R^3$ is tert.-butyl;

$R^4$ is carboxy or carboxy which can be converted into methyl ester;

A is methylene;

B is C=S, and

----- is single bond.

9. The compound or a salt thereof as claimed in claim 4, wherein $R^1$ is hydroxy;

$R^2$ is tert.-butyl;

$R^3$ is tert.-butyl;

$R^4$ is carboxy or carboxy which can be converted into methyl ester;

A is methylene;

B is $CH_2$, and

----- is single bond.

10. A compound of claim 4 having the following formula [I] or a salt thereof, $$\text{[I]}$$

wherein $R^1$ is hydroxy;

$R^2$ is lower alkyl;

$R^3$ is lower alkyl;

$R^4$ is carboxy, tetrazolyl or phosphono;

A is alkylene.

B is C=O, and

----- is single bond or double bond.

11. The compound or a salt thereof as claimed in claim 10, wherein $R^1$ is hydroxy;

$R^2$ is tert.-butyl;

$R^3$ is tert.-butyl;

$R^4$ is carboxy, tetrazolyl or phosphono;

A is methylene;.

B is C=O, and

----- is single bond or double bond.

12. The compound or a salt thereof as claimed in claim 2, wherein $R^1$ is hydroxy, lower alkanoyloxy or benzoyloxy.

13. The compound or a salt thereof as claimed in claim 2, wherein $R^1$ is hydroxy or lower alkanoyloxy.

14. The compound or a salt thereof as claimed in claim 2, wherein $R^1$ is hydroxy or acetyloxy.

15. The compound or a salt thereof as claimed in claim 2, wherein $R^1$ is hydroxy.

16. The compound or a salt thereof as claimed in claim 2, wherein $R^4$ is carboxy; carboxy which is converted into lower alkyl ester; carboxy which is converted into amide with ammonia or lower alkylamine; tetrazolyl; phosphono; phosphono which is converted into lower alkyl ester; sulfonyl; or sulfonyl which is converted into lower alkyl ester.

17. The compound or a salt thereof as claimed in claim 2, wherein $R^4$ is carboxy which can be converted into methyl or ethyl ester; carboxy which can be converted into amide with ammonia or methylamine; tetrazolyl; phosphono which can be converted into ethyl ester.

18. The compound or a salt thereof as claimed in claim 2, wherein $R^4$ is carboxy, tetrazolyl or phosphono.

19. The compound or a salt thereof as claimed in claim 2, wherein B is C=O.

20. The compound or a salt thereof as claimed in claim 2, wherein ⸺ is a single bond.

21. The compound or a salt thereof as claimed in claim 2, wherein ⸺ is a double bond.

22. The compound or a salt thereof as claimed in claim 2, wherein $R^1$ is hydroxy, lower alkanoyloxy or benzoyloxy;

$R^2$ is lower alkyl;

$R^3$ is hydrogen, lower alkyl, lower alkoxy, or substituted lower alkyl wherein the substituent is hydroxy, tetrahydropyranyloxy, amino or lower alkylamino.

23. The compound or a salt thereof as claimed in claim 2, wherein $R^1$ is hydroxy, lower alkanoyloxy or benzoyloxy;

$R^2$ is lower alkyl;

$R^3$ is hydrogen, lower alkyl or lower alkoxy.

24. The compound or a salt thereof as claimed in claim 2, wherein $R^1$ is hydroxy or acetyloxy;

$R^2$ is methyl, isopropyl or tert.-butyl;

$R^3$ is hydrogen, methyl, isopropyl, tert.-butyl or methoxy.

25. The compound or a salt thereof as claimed in claim 2, wherein $R^1$ is hydroxy;

$R^2$ is tert.-butyl;

$R^3$ is tert.-butyl.

26. 2-(3,5-Di-tert.-butyl-4-hydroxybenzylidene)-4-phosphonomethylthiomorpholine-3-one of claim 2.

27. 2-(3,5-Di-tert.-butyl-4-hydroxybenzylidene)-4-(1H-tetrazol-5-ylmethyl)-1,4-thiazine-3-one of claim 2.

28. 2-(3,5-Di-tert.-butyl-4-hydroxybenzylidene)-4-(1H-tetrazol-5-ylmethyl)thiomorpholine-3-one of claim 2.

29. 2-4-Carboxymethyl-2-(3,5-di-tert.-butyl-4-hydroxybenzylidene)-1,4-thiazine-3-one of claim 2.

30. 4-Carboxymethyl-2-(3,5-di-tert.-butyl-4-hydroxybenzylidene)thiomorpholine-3-one of claim 2.

31. A pharmaceutical composition which comprises a compound as claimed in claim 1 or salt thereof and pharmaceutically acceptable carrier.

32. A method for treatment of cataracts which comprises administering an effective amount to treat cataracts, of the composition as claimed in claim 31.

33. A compound having the following formula (II) or a salt thereof,

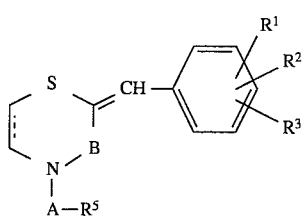

wherein $R^1$ is hydroxy or protected hydroxy;

$R^2$ is lower alkyl;

$R^3$ is hydrogen, lower alkyl, hydroxy, protected hydroxy, lower alkoxy, or substituted lower alkyl which is substituted by hydroxy, protected hydroxy, amino or lower alkylamino;

$R^5$ is cyano or lower alkoxy;

A is alkylene;

B is C=O, C=S or $CH_2$ and

⸺ is a single bond or a double bond.

34. A compound having the following formula (II) or a salt thereof,

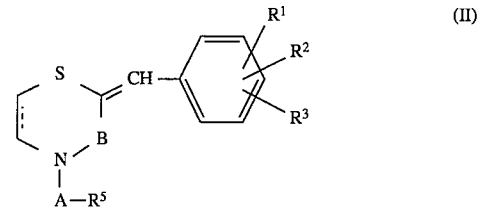

wherein $R^1$ is hydroxy, lower alkanoyloxy, lower alkylsulfonyloxy, arylsulfonyloxy, lower alkoxymethyloxy, benzoyloxy, benzyloxymethyloxy, tetrahydropyranyloxy or trimethylsilyloxy;

$R^2$ is lower alkyl;

$R^3$ is hydrogen, lower alkyl, hydroxy, lower alkanoyloxy, lower alkylsulfonyloxy, arylsulfonyloxy, lower alkoxymethyloxy, benzoyloxy, benzyloxymethyloxy, tetrahydropyranyloxy, trimethylsilyloxy, lower alkoxy or substituted lower alkyl which is substituted by hydroxy, lower alkanoyloxy, lower alkylsulfonyloxy, arylsulfonyloxy, lower alkoxymethyloxy, benzoyloxy, benzyloxymethyloxy, tetrahydropyranyloxy, trimethylsilyloxy, amino or lower alkylamino;

$R^5$ is cyano or lower alkoxy;

A is alkylene;

B is C=O, C=S or $CH_2$ and

⸺ is a single bond or a double bond.

35. The compound as claimed in claim 34 or a salt thereof, wherein $R^1$ is hydroxy, lower alkanoyloxy, lower alkoxymethyloxy or benzoyloxy;

$R^2$ is hydrogen, lower alkyl, lower alkoxy or substituted lower alkyl which is substituted by hydroxy, tetrahydropyranyloxy, amino or lower alkylamino; and B is C=O.

36. A compound of claim 34 having the following formula [II] or a salt thereof,

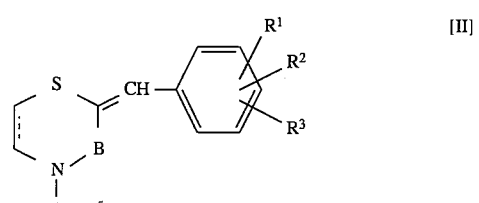

wherein $R^1$ is hydroxy, lower alkanoyloxy or lower alkoxymethyloxy;

$R^2$ is lower alkyl;

$R^3$ is hydrogen or lower alkyl;

$R^4$ is cyano or lower alkoxy;

A is alkylene;

B is C=O, and

⸺ is single bond or double bond.

37. The compound as claimed in claim 36 or a salt thereof, wherein $R^1$ is hydroxy, acetyloxy or methoxymethoxy;

$R^2$ is methyl, isopropyl or tert.-butyl;
$R^3$ is hydrogen, methyl, isopropyl or tert.-butyl;
$R^5$ is cyano or methoxy;
A is methylene or ethylene.

38. 2-(3,5-Di-tert.-butyl-4-methoxymethoxybenzylidene)-4-methoxymethylthiomorpholine- 3-one of claim 34.

39. 4-Cyanomethyl-2-(3,5-di-tert.-butyl-4-hydroxybenzylidene)- 1,4-thiazine-3-one of claim 34.

40. 4-Cyanomethyl-2-(3,5-di-tert.-butyl-4-hydroxybenzylidene)thiomorpholine- 3-one of claim 34.

* * * * *